US00RE43497E

(19) United States
(12) Reissued Patent
Brunner et al.

(10) Patent Number: US RE43,497 E
(45) Date of Reissued Patent: Jun. 26, 2012

(54) ANTI-MIF ANTIBODIES

(75) Inventors: Herwig Brunner, Weilheim (DE); Jürgen Bernhagen, Aachen (DE); Robert Kleemann, Leiden (NL); Ralf Mischke, Biberach (DE); Afroditi Kapurniotu, Aachen (DE)

(73) Assignee: Fraunhofer-Gesellschaft zur Forderung der Angewandten Forschung E.V., Munich (DE)

(21) Appl. No.: 12/234,407

(22) Filed: Sep. 19, 2008

Related U.S. Patent Documents

Reissue of:
(64) Patent No.: 7,303,885
Issued: Dec. 4, 2007
Appl. No.: 10/148,496
PCT Filed: Nov. 2, 2000
PCT No.: PCT/EP00/10814
§ 371 (c)(1),
(2), (4) Date: Sep. 13, 2002
PCT Pub. No.: WO01/38566
PCT Pub. Date: May 31, 2001

(30) Foreign Application Priority Data

Nov. 26, 1999 (DE) ..... 199 57 065

(51) Int. Cl.
*C07K 16/00* (2006.01)

(52) U.S. Cl. ..... 530/388.23; 435/4; 435/7.1; 435/7.4; 435/25; 435/29; 435/189; 436/86; 436/501; 436/503; 436/504; 530/350; 530/358; 530/388.24; 530/389.2; 530/413

(58) Field of Classification Search ..... None
See application file for complete search history.

(56) References Cited

U.S. PATENT DOCUMENTS

| | | | | |
|---|---|---|---|---|
| 5,595,885 | A | 1/1997 | Stetler-Stevenson et al. | |
| 5,599,677 | A * | 2/1997 | Dowell et al. | 435/7.4 |
| 5,716,595 | A * | 2/1998 | Goldenberg | 424/1.49 |
| 7,294,753 | B2 * | 11/2007 | Kloetzer et al. | 800/4 |

FOREIGN PATENT DOCUMENTS

| | | | |
|---|---|---|---|
| WO | WO 96/32503 | | 10/1996 |
| WO | WO-97-00959 | A1 | 1/1997 |
| WO | WO-97-41206 | A2 | 11/1997 |
| WO | WO 98/17314 | | 4/1998 |
| WO | WO 99/24574 | | 5/1999 |
| WO | WO 99/42578 | | 8/1999 |
| WO | WO-02-36774 | A2 | 5/2002 |

OTHER PUBLICATIONS

E.E. Conn et al, Outlines of Biochemistry, Fourth Edition, John Wiley & Sons, Inc., 1976, p. 88.*
Gerritsen et al., "Partial amino acid sequence of purified von Willebrand factor-cleaving protease," Blood 98:1654-1661 (2001).*
Burger-Kentischer et al., "Binding of JAB1/CSN5 to MIF is mediated by the MPN domain but is independent of the JAMM motif," FEBS Lett. 579(7):1693-1701 (2005).
Kleemann et al., "Disulfide analysis reveals a role for macrophage migration inhibitory factor (MIF) as thiol-protein oxidoreductase," J Mol Biol. 280(1):85-102 (1998).
Kleemann et al., "Intracellular action of the cytokine MIF to modulate AP-1 activity and the cell cycle through Jab1," Nature 408(6809):211-216 (2000).
Li et al., "Macrophage migration inhibitory factor directly interacts with hepatopoietin and regulates the proliferation of hepatoma cell;" Exp. Cell Res. 300(2):379-87 (2004).
Lue et al., "Macrophage migration inhibitory factor (MIF) promotes cell survival by activation of the Akt pathway and role for CSN5/JAB1 in the control of autocrine MIF activity," Oncogene 26(35):5046-5059 (2007).
Lue et al., "Rapid and transient activation of the ERK MAPK signalling pathway by macrophage migration inhibitory factor (MIF) and dependence on JAB1/CSN5 and Src kinase activity," Cell Signal. 18(5):688-703 (2006).
EP08008867.7 Official Action dated Oct. 20, 2009.
Apr. 21, 2010 Response to Oct. 20, 2009 EP08008867.7 Official Action.
EP08008867.7 Search Report dated Jan. 28, 2009.
EP08008874.3 Official Action dated Mar. 4, 2009.
Sep. 14, 2009 Response to Mar. 4, 2009 EP08008874.3 Official Action.
EP08008874.3 Official Action dated Oct. 27, 2009.
May 10, 2010 Response to Oct. 27, 2009 EP08008874.3 Official Action.
EP08008874.3 Search Report dated Oct. 13, 2008.
Dec. 30, 2008 Response to EP08008874.3 Search Report.
Notice of and Grounds for Opposition to EP Patent 1346034 dated Mar. 20, 2009.
Furlan et al., "Deficient Activity of von Willebrand Factor-Cleaving Protease in Chronic Relapsing Thrombotic Thrombocytopenic Purpura," Blood 89:3097-3103 (1997).
Furlan et al., "Partial Purification and Characterization of a Protease From Human Plasma Cleaving von Willebrand Factor to Fragments Produced by In Vivo Proteolysis," Blood 87(10):4223-4234 (1996).
Claret et al., "A new group of conserved coactivators that increase the specificity of AP-1 transcription factors," Nature 383 (6599):453-457 (1996).
Kleemann et al., "Characterization of catalytic centre mutants of macrophage migration inhibitory factor (MIF) and comparison to Cys81Ser MIF," Eur J Biochem 261(3):753-766 (1999).
EP00981235.5 Decision revoking EP-B-1235934 dated May 19, 2011.

* cited by examiner

*Primary Examiner* — David A Saunders
(74) *Attorney, Agent, or Firm* — Wilson, Sonsini, Goodrich & Rosati

(57) ABSTRACT

The present invention relates to methods for screening molecules and methods to detect protein-protein interactions and means used therein. More specifically, the present invention relates to methods for screening candidate drugs for treating or detecting MIF (macrophage migration inhibitor factor) related diseases. In certain aspects, the present invention involves detecting MIF/Jab1 (c-Jun activation domain binding protein) interactions as a basis for modulating cellular regulatory pathways and for identifying candidate drugs for MIF-related diseases. The invention also provides methods for the identification of molecules which dissociate or prevent interaction or binding between MIF and Jab1.

8 Claims, 13 Drawing Sheets

MIF specifically interacts with Jab1 (1)

a b

MIF-bead pull-down/
Anti-Jab1 Western

MIF specifically interacts with Jab1 (2)

MIF inhibits potentiation of AP-1 reporter gene activity by Jab1 (1)

a b c

Modulation of JNK by Jab1 and MIF

Mechanism of Kip1 induction by MIF (1)

Characterisation of the binding site between MIF and Jab1 (1):

Involvement of the region (50-65) of MIF

Characterisation of the binding site between MIF and Jab1 (2):

Mutant C60SMIF shows reduced p27Kip1-inducing properties

C

Effect of MIF on growth of fibroblasts (1)

Effect of MIF on growth of fibroblasts (2)

ANTI-MIF ANTIBODIES

Matter enclosed in heavy brackets [ ] appears in the original patent but forms no part of this reissue specification; matter printed in italics indicates the additions made by reissue.

CROSS-REFERENCE TO RELATED APPLICATIONS

This application is *reissue of U.S. application Ser. No. 10/148,496, filed Sep. 13, 2002, now U.S. Pat. No. 7,303,885, which is* a U.S. National Stage Application under 35 U.S.C. §371 of PCT International Application No. PCT/EP00/10814, filed Nov. 2, 2000, which claims priority to German Patent Application 199 57 065.5, filed Nov. 26, 1999. Each of these applications is incorporated herein by reference as if set forth in its entirety.

*This application contains references to amino acid sequences which were submitted on Jul. 2, 2009 as the sequence listing text file "36591704998.TXT", file size 2 MegaBytes (MB), created on Jul. 1, 2009. The aforementioned sequence listing is hereby incorporated by reference in its entirety pursuant to 37 CFR §1.52(e)(5).*

The present invention relates to screening methods for candidate drugs effective in treating or detecting MIF (macrophage migration inhibitory factor) related diseases, and means used therein.

In response to antigenic or mitogenic stimulation, lymphocytes secret protein mediators called lymphokines that play an important role in immunoregulation, inflammation, stress response, and effector mechanisms of cellular immunity. The first reported lymphokine activity was observed in culture supernatants of antigenically sensitised and activated guinea pig lymphocytes. This activity was named migration inhibitory factor (MIF) for its ability to prevent the migration of guinea pig macrophages out of capillary tubes in vitro. MIF has also been identified as a secretable product of macrophages, anterior pituitary cells and endothelial cells activating both macrophages and T-lymphocytes and certain other cell types.

The detection of MIF activity is correlated with a variety of inflammatory responses including delayed hypersensitivity and cellular immunity, allograft rejection, rheumatoid polyarthritic synovialis, and autoimmune diseases. In addition, MIF has enzymatic activity, showing both tautomerase and thiol-protein oxidoreductase activity. MIF has various proinflammatory properties. In this function, MIF was demonstrated to be a mediator of several inflammatory diseases including Gram-negative and Gram-positive septic shock, adult respiratory distress syndrome, and its pro-inflammatory properties are due in part to its capacity to induce the release of other proinflammatory cytokines, such as interleukin-1, tumour necrosis factor and by the counterregulation of glucocorticoid action. MIF also plays a role in the regulation of cellular redox homeostasis. Despite functional similarities with other cytokines, MIF exhibits a number of characteristic features. For example, MIF expression is not restricted to cells of the immune and endocrine systems and MIF protein is found preformed in most MIF-expressing cells.

Although of tremendous importance for the development of diagnostic and therapeutic tools for MIF-related diseases, the molecular targets of MIF action have not been identified; MIF could have direct intracellular functions based on interactions with intracellular proteins. Molecules—so-called drugs—which disrupt, prevent, enhance or modulate interaction of MIF with other proteins can influence the key role of MIF in cell cycle control, immuno-modulation, redox-effects and regulatory pathways.

WO 99/42578 describes methods and reagents for extending the lifespan, e.g. the number of mitotic divisions, of a cell by use of MIF or a homologe thereof which induces cell proliferation. This document also describes the treatment of proliferative disorders by inhibiting MIF induced bypass of the p53 cell cycle checkpoints. The document describes that MIF is the first example of a natural protein capable of functionally inactivating the growth arrest phenotype of a tumor-suppressor in trans. In addition, since MIF has been identified as having a pro-inflammatory role, both systematically and locally, this observation provides a link between the fields of inflammation and tumor biology.

WO 98/17314 describes a method of treating or preventing a disease which involves [celloverproliferation] *cell overproliferation* in a subject comprising administering to a subject in which such treatment or prevention is desired [as] *a* therapeutically effective amount of a[.] MIF antagonist agent. Furthermore, there is disclosed a method for treating [tumor-neovascularisation] *tumor neovascularization* in a subject, comprising administering a therapeutically effective amount of an agent which inhibits or [neutralises] *neutralizes* the activity of MIF. Agents for [neutralising] *neutralizing* the activity of MIF are, for example, anti-MIF[-] monoclonal antibodies, MIF antisense RNA molecules and combinations thereof.

In principle, the interaction of MIF with other proteins can be tested with a two-hybrid system. The yeast two-hybrid system has been used to detect the association of pairs of proteins (see, e.g., Fields et al., U.S. Pat. No. 5,283,173). This method involves in vivo reconstitution of two separable domains of a transcription factor. The DNA binding domain of the transcription factor is required for recognition of a chosen promoter. The activation domain is required for contacting other components of the cell's transcriptional machinery. In this system, the transcription factor is reconstituted through the use of hybrid proteins. One hybrid is composed of the activation domain and a first protein of interest. The second hybrid is composed of the binding domain and a second protein of interest. In cases where the first and second proteins of interest interact with each other, the activation domain and binding domain are brought into close physical proximity, thereby reconstituting the transcription factor. Association of the proteins can be measured by assaying the ability of the reconstituted transcription factor to activate transcription of a reporter gene.

Methods and compositions for drug screening are known (U.S. Pat. No. 5,569,588). A method for modelling the transcriptional responsiveness of an organism to a candidate drug involves for instance (a) detecting reporter gene product signals from each of a plurality of different, separately isolated cells of a target organism, wherein each cell contains a recombinant construct comprising a reporter gene operatively linked to a different endogenous transcriptional regulatory element of the target organism such that the transcriptional regulatory element regulates the expression of the reporter gene, and the sum of the cells comprises an ensemble of the transcriptional regulatory elements of the organism sufficient to model the transcriptional responsiveness of the organism to a drug; (b) contacting each cell with a candidate drug; (c) detecting reporter gene product signals from each cell; (d) comparing reporter gene product signals from each cell before and after contacting the cell with the candidate drug to obtain a drug response profile which provides a model of the transcriptional responsiveness of the organism to the candidate drug.

Thus, it is considered particularly important to develop and provide methods and means that allow (i) the detection of the interaction of MIF with an intracellular target molecule, for instance a protein and (ii) the identification of molecules which modify this interaction of MIF with the intracellular target molecule.

Thus, the technical problem underlying the present invention is to provide means and methods for screening drugs effective in diagnosing and treating MIF-related diseases.

The present invention solves this problem by providing a method for screening candidate drugs effective in diagnosing and treating MIF-related diseases by testing whether the candidate drug disrupts interaction, in particular, binding between MIF and Jab1, and/or interferes with a MIF/Jab1-specific cellular effect, the method comprising detecting in a MIF and Jab1 system an interaction between MIF and Jab1 and/or a MIF/Jab1-specific cellular effect in the absence of a candidate drug, and comparing the detected interaction and/or cellular effect to an interaction and/or cellular effect detected in a system containing MIF and Jab1 in the presence of a candidate drug and whereby the detected and compared interactions and/or cellular effects are preferably specific MIF/Jab1 complex based biological effects.

Thus, the present invention is inter alia based on the finding that MIF and Jab1 interact, in particular bind to each other and thus form a MIF/Jab1 complex. A wide variety of medical applications in which MIF-Jab1-complexes play an important role are encompassed by the present invention e.g. cell growth-related diseases in general, in particular the method of the invention may be used to determine and find drugs for the treatment of MIF-related diseases: endogenous uveitis, proteinuria, glomerulonephritis, wound repair, carcinogenesis, tinnitus, septic shock and arthritis etc.

The interaction between MIF and Jab1 demonstrates that a cytokine can modulate cellular regulatory pathways by direct interaction with a transcriptional co-activator. MIF-Jab1 interaction provides a molecular basis for prominent activities of MIF.

Jab1 (c-Jun activation domain binding protein), in particular $p38^{Jab1}$, is a 38K protein originally identified as a specific co-activator of the c-Jun and JunD transcription factors, and which also acts as a negative regulator of the cyclin-dependent-kinase (CDK) inhibitor $p27^{Kip1}$. A transcriptional co-activator function of Jab1 is due to enhancement of AP-1-dependent transcriptional activity. Jab1 homologues have also been identified in plants, whereby the plants homologue of Jab1 are also involved in the regulation of AP-1 transcription factor activity (WO 99/24574). Jab1 is a member of the Mov34 family of proteins (Hofmann and Bacher, 1998; Asano et al., 1997). MIF inhibits enhancement of AP-1 transcriptional activity by Jab1. Jab1 is identified to activate c-Jun N-terminal kinase activity (JNK) and this effect is markedly down-regulated by MIF. MIF according to the present invention blocks Jab1- and TNF-mediated activation of JNK. In accordance with the present invention MIF also counter-regulates Jab1 dependent cell cycle processes. MIF increases $p27^{Kip1}$ expression by stabilisation of $p27^{Kip1}$ protein and inhibits Jab1 mediated rescue of fibroblasts from starvation induced growth arrest. MIF colocalises with Jab1 in the cytosol and both endogenously expressed and exogenous MIF following endocytosis and being targeted to the cytosol bind Jab1 in the cytosol. MIF inhibits Jab1- and stimulus-enhanced AP-1 activity, but does not interfere with induction of NFκB. Jab1 activates JNK activity and enhances endogenous phospho-c-Jun levels and MIF inhibits these effects. MIF also antagonises Jab1-dependent cell cycle regulation by increasing $p27^{Kip1}$ expression through stabilisation of $p27^{Kip1}$ protein. Consequently, Jab1-mediated rescue of fibroblasts from growth arrest is blocked by MIF. Analysis of a MIF peptide consisting only of residues 50-65 of wild-type MIF and of a mutant Cys60 (wildtype MIF with Cys at position 60) shows that region 50-65 is important for Jab1 binding and modulation. MIF may broadly act to negatively regulate Jab1-controlled pathways and MIF/Jab1 interaction could provide a long sought molecular basis for key activities of MIF. MIF broadly acts to negatively regulate Jab1-controlled cellular pathways. The MIF-Jab1 interaction provides a molecular basis for key activities of MIF because the MIF-Jab1 interaction is connected with pathways and cellular and molecular cycles in the context of MIF-related diseases.

In the context of the present invention, a number of general terms shall be utilised as follows.

In the context of the present invention, a "MIF-related disease" is a disease such as arthritis, carcinogenesis and/or cancer, nephritis, proteinuria, dermatitis, diabetes/obesity, acute and chronic renal allograft rejection, tubulitis, degeneration of neurones, Parkinson's disease, septic shock, endotoxemia, hypersensitivity, uveitis, tinnitus, wound repair/cell growth; MIF also plays an important role in immunoregulation, inflammation and effector mechanisms of cellular and humoral immunity, septic shock, ocular inflammation, in the regulation of transcriptional and cell cycles, and respiratory distress syndrome, physiological stress and others.

In the context of the present invention, the term "drug" refers to a substance being useful for diagnosing and/or treating diseases, in particular MIF-related diseases, preferably in an amount sufficient to obtain such an effect. As used herein, the term "drug" refers both to the active agent itself and the active agent in connection with pharmaceutically acceptable carriers, adjuvants, other active agents, etc. A putative or candidate drug is meant to be a substance or composition to be tested as to whether this substance or composition is suitable to be used as a drug. In a particularly preferred embodiment a "drug" is a small MIF-derived peptide, in particular MIF 50-65 or $57^{Ser}$ $60^{Ser}$ MIF 60-65. Thus, the present invention also encompasses the specific peptides which are depicted in SEQ ID No's 1 and 2.

In the context of the present invention, the term "treatment" refers to the prophylacetic and/or therapeutic effect of a drug.

In the context of the present invention, a "MIF and Jab1 system" relates to a system in which synthetically produced or naturally occurring MIF and Jab1 are present under conditions which permit that they contact each other and bind, either under natural or artificial conditions. In one embodiment of the present invention, a MIF and Jab1 system is a naturally occurring cell or a recombinantly produced cell. In another embodiment of the present invention, a MIF and Jab1 system may be a crude extract made from the above cells or made from other sources, as long as they contain MIF and Jab1. In another embodiment of the present invention, a MIF and Jab1 system is for instance an in vitro translation system containing elements allowing the production or purification of pure or semi-pure MIF and Jab1 or of fusion or complex proteins comprising all or a part of MIF and Jab1, each alone or together.

In the context of the present invention, the term "MIF" relates to naturally occurring MIF as well as to any modifications, mutants or derivatives of MIF such as recombinantly produced MIF containing amino acid modifications, such as inversions, deletions, insertions, additions, etc., as long as at least part of the essential biological functions of wildtype MIF are present. Such a MIF may also comprise unusual amino acids and/or modifications such as alkylation, oxidation, thiol-modification, denaturation, and oligomerisation and the like. In particular, in the context of the present invention, a MIF may be a protein, in particular a fusion protein containing all or part of the MIF in addition to other proteins, peptides or parts thereof. In a further embodiment of the present invention, the MIF is a truncated version of the naturally occurring MIF, such as a small peptide. In a particularly preferred embodiment of the present invention, such a small peptide is a MIF peptide fragment such as MIF 50-65 (peptide consisting of wildtype amino acid sequence residues 50-65 (SEQ ID No. 1) or $Ser^{57}$ $Ser^{60}$ MIF 50-65 (wildtype amino acid residues 50-65 except for the replacement of wildtype Cys 57 and Cys 60 by $Ser^{57}$ and $Ser^{60}$.) Both of these peptides are subject matter of the present teaching.

In the context of the present invention, the term "Jab1" relates to naturally occurring Jab1 as well as to any modifications, mutants or derivatives of Jab1 such as recombinantly produced Jab1 containing amino acid modifications, such as inversions, deletions, insertions, additions, etc., as long as at least part of the essential biological functions of wildtype Jab are present. Such a Jab1 may also comprise unusual amino acids and/or modifications such as alkylation, oxidation, thiol-modification, denaturation, and oligomerisation and the like. In particular, in the context of the present invention, a Jab1 may be a protein, in particular a fusion protein containing all or part of the Jab1 in addition to other proteins, peptides or parts thereof. In a further embodiment of the present invention, the Jab1 is a truncated version of the naturally occurring Jab1 such as the so-called MPN domain or Mov-34 domain (Asano et al., 1997; Hofmann and Bacher, 1998) or a small peptide.

The term "promoter" refers to a sequence of DNA, usually upstream (5') to the coding sequence of a structural gene, which controls the expression of the coding region by providing the recognition for RNA polymerase and/or other factors required for transcription to start at the correct site. Promoter sequences are necessary, but not always sufficient to drive the expression of the gene.

"Nucleic acid" refers to a large molecule which can be single or double stranded, composed of monomers (nucleotides) containing a sugar, phosphate and either a purine or pyrimidine. The nucleic acid may be cDNA, genomic DNA, or RNA, for instance mRNA.

The term "nucleic acid sequence" refers to a natural or synthetic polymer of DNA or RNA which may be single or double stranded, alternatively containing synthetic, non-natural or altered nucleotide bases capable of incorporation into DNA or RNA polymers.

The term "gene" refers to a DNA sequence that codes for a specific protein and regulatory elements controlling the expression of this DNA sequence.

The term "coding sequence" refers to that portion of a gene encoding a protein, polypeptide, or a portion thereof, and excluding the regulatory sequences which drive the initiation or termination of transcription. The coding sequence and/or the regulatory element may be one normally found in the cell, in which case it is called "autologous" or "endogenous", or it may be one not normally found in a cellular location, in which case it is termed "heterologous".

A heterologous gene may also be composed of autologous elements arranged in an order and/or orientation not normally found in the cell in which it is transferred. A heterologous gene may be derived in whole or in part from any source known to the art, including a bacterial or viral genome or episome, eucaryotic nuclear or plasmid DNA, cDNA or chemically synthesised DNA. The structural gene may constitute an uninterrupted coding region or it may include one or more introns bounded by appropriate splice junctions. The structural gene may be a composite of segments derived from different sources, naturally occurring or synthetic.

A "transactivator protein" is a protein that can bind to the operator region of a gene and thereby promote transcription of the gene.

A "DNA-binding domain" is a sequence of amino acids that are capable of binding to a specific DNA sequence.

A "fusion protein" is a protein made up of amino acid sequences derived from at least two different sources. In the context of a fusion protein, a "heterologous" amino acid sequence is a sequence originating from a source different from other parts of the fusion protein.

A "detectable gene product" is a nucleotide or amino acid sequence that can be detected by an assay. Preferably, the expression of a detectable gene product confers a characteristic on a cell that allows the cell to be conveniently selected among other cells that do not express the detectable gene product.

By "operably linked" or "under operational control" it is meant that a gene and a regulatory sequence are connected in sense or antisense expression in such a way as to permit gene expression when the appropriate molecules (e.g. transcriptional activator proteins) are bound to the regulatory sequence.

The term "associated" in the context of the present invention refers to any type of interaction between MIF and Jab1, in particular covalent or non-covalent binding or association such as, but not limited to, a covalent bond, hydrophobic/hydrophilic interaction, van der Waals forces, ion pairs, ligand-receptor interaction, epitope-antibody binding site interaction, enzyme-substrate interaction, liposome-hydrophobic interaction, nucleotide base pairing, membrane-hydrophobic interaction, and the like. Such an association may also include the presence of further molecules, such as peptides, proteins, such as Kip, Jun, c-Jun-amino-terminal kinase (JNK), steroid receptor coactivator 1 (SRC-1), integrin LFA-1, progesterone receptor (PR) or glucocorticoide receptor (GR), or nucleotide sequences.

The term "vector" refers to a recombinant DNA construct which may be a plasmid, virus, or autonomously replicating sequence, phage or nucleotide sequence, linear or circular, of a single or double stranded DNA or RNA, derived from any source, in which a number of nucleotide sequences have been joined or recombined into a unique construction which is capable of introducing a promoter fragment and DNA sequence for a selected gene product in sense or antisense orientation along with an appropriate 3' untranslated sequence into a cell.

"Plasmids" are genetic elements that are stably inherited without being a part of the chromosome of their host cell. They may be comprised of DNA or RNA and may be linear or circular. Plasmids code for molecules that ensure their replication and stable inheritance during cell replication and may encode products of considerable medical, agricultural and environmental importance. For example, they code for toxins that greatly increase the virulence of pathogenic bacteria. They can also encode genes that confer resistance to antibiotics. Plasmids are widely used in molecular biology as vectors to clone and express recombinant genes. Plasmids are generally designated herein by a lower case p preceded and/or followed by upper-case letters and/or numerals, in accordance with standard naming conventions familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "expression" as used herein is intended to describe the transcription and/or coding of the sequence for the gene product. In the expression, a DNA chain coding for the sequence of gene product is first transcribed to a complementary RNA, which is often an mRNA, and then the thus transcribed mRNA is translated into the above mentioned gene product if the gene product is a protein. However, expression also includes the transcription of DNA inserted in antisense orientation to its regulatory elements. Expression, which is constitutive and possibly further enhanced by an externally controlled promoter fragment thereby producing multiple copies of mRNA and large quantities of the selected gene product, may also include overproduction of a gene product.

The term "host cell" refers to a cell which has been genetically modified by transfer of a chimeric, heterologous or autologous nucleic acid sequence or its descendants still containing this sequence. These cells are also termed "transgenic cells". In the case of an autologous nucleic acid sequence being transferred, the sequence will be present in the host cell in a higher copy number, in a different orientation and/or at a different place than naturally occurring.

The term "MIF-Jab1-complex" refers to an association of MIF and Jab1, e.g. an interaction between domains of MIF and Jab1.

The term "target activity" refers to a MIF-Jab1-complex induced activity, e.g. an expression of a reporter gene or a regulation of an AP-1 activity or a regulation of CDK (cyclin-dependent kinases) inhibitors or other MIF-Jab1-specific target activities.

The proteins of the invention that do not occur in their natural (cellular) environment are isolated. The term "isolated" as used herein, in the context of proteins, refers to a polypeptide which is unaccompanied by at least some of the material with which it is associated in its natural state. The isolated protein constitutes at least 0.5%, preferably at least 5%, more preferably at least 25% and still more preferably at least 50% by weight of the total protein in a given sample. Most preferably the "isolated" protein is substantially free of other proteins, lipids, carbohydrates or other materials with which it is naturally associated, and yields a single major band on a non-reducing polyacrylamide gel. Substantially free means that the protein is at least 75%, preferably at least 85%, more preferably at least 95% and most preferably at least 99% free of other proteins, lipids, carbohydrates or other materials with which it is naturally associated.

"Affinity chromatography" is known to involve separation of proteins by selective absorption onto and/or elution from a solid medium or a solid support (e.g. immobilised Jab1, immobilised MIF, immobilised anti-MIF-Jab1-domain antibodies and/or immobilised anti-MIF-Jab1-fusion-protein antibodies etc.), generally in the form of a column. The solid medium is usually an inert carrier matrix to which is attached a ligand having the capacity to bind under certain conditions with the required protein or proteins in preference to others present in the same sample, although in some cases the matrix itself may have such selective binding capacity. The ligand may be biologically complementary to the protein to be separated, for example, anti-gen and antibody, or may be any biologically unrelated molecule which by virtue of the nature and steric relationship of its active groups has the power to bind the protein. The support matrices commonly used in association with such protein-binding ligands include, for example, polymers and copolymers of agarose, dextrans and amides, especially acrylamide, or glass beads or nylon matrices. Cellulose and substituted celluloses are generally found unsuitable when using dyes, since, although they bind large amounts of dye, the dye is poorly accessible to the protein, resulting in poor protein binding.

By "solid support" an insoluble matrix is meant, either biological in nature, such as, without limitation, a cell or bacteriophage particle, or synthetic, such as, without limitation, an acrylamide derivate, cellulose, nylon, silica and magnetised particles, to which soluble molecules may be linked or joined.

"Antibody" refers to a polypeptide substantially encoded by an immunoglobulin gene or immunoglobulin genes, or fragments thereof, which specifically bind and recognise an analyte (antigen). The recognised immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well characterised fragments produced by digestion with various peptidases. "Antibody" also refers to modified antibodies (e.g. oligomeric, reduced, oxidated and labelled antibodies). The term "antibody", as used herein, also includes antibody fragments either produced by the modification of whole antibodies or those synthesised de novo using recombinant DNA methodologies. The term "antibody" includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York (1988)).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Monoclonal antibodies to the proteins of the present invention, and to the fragments thereof, can also be readily produced by one skilled in the art. The general methodology for making monoclonal anti-bodies by using hybridoma technology is well known Immortal antibody-producing cell lines can be created by cell fusion, and also by other techniques such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980); see also U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against the protein of interest, or fragment thereof, can be screened for various properties; i.e., for isotype, epitope, affinity, etc. Alternatively, genes encoding the monoclonals of interest may be isolated from the hybridomas by PCR techniques known in the art and cloned and expressed in the appropriate vectors. Monoclonal antibodies are useful in purification, using immunoaffinity techniques of the individual proteins against which they are directed. The antibodies of this invention, whether polyclonal or monoclonal, have additional utility in that they may be employed as reagents in immunoassays, RIA, ELISA, and the like. In addition, they can be used to isolate the MIF, Jab1, MIF-Jab1 domain etc. from cells. The antibodies e.g. could be used to establish a tissue culture based assay for discovery or modification of novel compounds which block the interaction of MIF and Jab1.

The humanised or chimeric antibodies can comprise portions derived from two different species (e.g., human constant region and murine binding region). The portions derived from two different species can be joined together chemically by conventional techniques or can be prepared as a single fusion protein using genetic engineering techniques. DNA encoding the proteins of both portions of the chimeric antibody can be expressed as a single fusion protein.

An antibody "specifically binds to" or "is specifically immunoreactive with" a protein when the antibody functions in a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solidphase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

"Immunoassay" refers to an assay that utilises an antibody to specifically bind an analyte. The immunoassay is characterised by the use of specific binding properties of a particular antibody to isolate, target, and/or quantify the analyte.

In a preferred embodiment of the present invention, the method for drug-screening is an in vitro method.

In a particularly preferred embodiment of the present invention, the in vitro method for [drugscreening] *drug-screening* is an assay for detecting the interaction, in particular binding between MIF and Jab1.

In a preferred embodiment of the present invention, the MIF-Jab1 binding is measured by using conventional methods of radioactive labelling, photo labelling, fluorescence labelling, biotin labelling, co-precipitation, immunoprecipitation, fractionation by chromatography etc. of MIF, Jab1 and/or the complex thereof in the presence or absence of a drug to be screened.

In particular, the present invention relates to so-called HTP methods, this means high throughput screening methods. In accordance with one embodiment of the present invention, MIF/Jab1 binding may be tested in the presence or absence of a competitive peptide which competes with MIF or Jab1 for the respective binding partner, i.e. MIF or Jab1. In particular, such a competitive binding partner may be a MIF derived analogue, for instance, a mutant of MIF, e.g. a fragment of MIF such as a peptide fragment consisting of amino acid residues 50-65 of wildtype human MIF or a peptide fragment consisting of wildtype amino acid residues 50-65 of human MIF except that at positions 57 and 60, with respect to the wildtype numbering (Kleemann et al., 1998 b) the natural occurring amino acids have been replaced by Ser. Thus, these truncated 16 amino acid residues long MIF peptides are, according to the present invention, very useful MIF competitive peptides which might be used in the present assay systems. In particular, in a further preferred embodiment of the present invention, MIF/Jab1 binding can be tested in the presence or absence of such a competitive peptide, while simultaneously, a candidate drug is also present to be tested for its effects on MIF/Jab1 interaction. In another preferred embodiment the above identified MIF truncated peptides may serve itself as candidate drugs, i.e. eventually as drugs.

Such a competitive binding partner may also be a Jab1 derived analogue, for instance, a mutant of Jab1 or a fragment of Jab1 such as a domain or peptide fragment of wildtype human or mouse Jab1. Such truncated Jab1 proteins or peptides are, according to the present invention, very useful Jab1 competitive molecules which might be used in the present assay systems. In particular, in a further preferred embodiment of the present invention, MIF/Jab1 binding can be tested in the presence or absence of such a competitive Jab1 peptide, while simultaneously, a candidate drug is also present to be tested for its effects on MIF/Jab1 interaction. In another preferred embodiment these Jab1 truncated molecules may serve itself as candidate drugs, i.e. eventually as drugs.

In a preferred embodiment of the present invention, the binding between MIF and Jab1 can, for instance, be explored by co-precipitation: MIF is immobilised on beads either covalently or non-covalently via e.g. binding of GST-MIF to GSH-beads or biotin-MIF to Streptavidin beads or MBP-MIF to malate beads (MBP: malate binding protein) and incubated with soluble Jab1 in the absence (control) and presence of candidate drugs. The suspension is washed and the amounts of Jab1 bound to the solid phase are detected by Western-Blot or the like following elution of Jab1 from the complex or Jab1 is detected in the supernatant; the amounts of Jab1 in the presence and absence of candidate drugs are compared.

The binding between Jab1 and MIF can also, for instance, be investigated by co-precipitation: Jab1 is immobilised on beads and incubated with soluble MIF in the absence (control) and presence of drugs. Jab may be bound either covalently or non-covalently to the beads via e.g. binding or binding of GST-Jab1 to GSH-beads or biotin-Jab1 to Streptavidin beads or binding of MBP-Jab1 to malate beads. The suspension is washed and the amounts of MIF bound to the solid phase are detected e.g. by Western-Blot or the like following eluation of MIF from the complex or MIF is detected in the supernatant; the amounts of MIF in the presence and absence of putative or candidate drugs are compared.

The general concept of these co-precipitation embodiments is incubation of two partners, for instance Jab1 and MIF, whereby one partner, for instance MIF, is covalently bound to GST. The two partners, MIF-GST and Jab1 were incubated in the presence of a solid phase, for instance GSH-beads. In this way the complex of MIF and Jab1 can bind to the GSH-beads because a non-covalent binding between GSH and GST which is covalently bound to MIF occurs. The suspension of solid phase-GSH-beads- and the non-covalent bound complex of GST-MIF which is non-covalent bound to Jab1 is washed and then Jab1 is eluated by boiling in SDS buffer. The supernatant of the suspension is separated by SDS-PAGE. The SDS gel is blotted by Western-Blot and Jab1 is detected on the blot by anti-Jab1 antibodies.

From this general concept various embodiments are preferred:

(i) GSH-beads were incubated with GST-MIF and Jab1; and Jab1 bound to GSH-beads via GST-MIF (see above) is detected with anti-Jab1 antibodies by Western-Blot, (ii) MIF-beads were incubated with Jab1; and Jab1 bound to the MIF-beads is detected with anti-Jab1 antibodies by Western-Blot, (iii) GSH-beads were incubated with GST-Jab1 and MIF; and MIF bound to GSH-beads via GST-Jab1 is detected with anti-MIF antibodies by Western-Blot, (iv) Jab1-beads were incubated with soluble MIF; and MIF bound to Jab1-beads is detected with anti-MIF antibodies by Western-Blot, (v) Malate-beads were incubated with MBP-MIF and Jab1; and Jab1 bound to Malate-beads via MBP-MIF is detected with anti-Jab1 antibodies by Western-Blot, (vi) Malate-beads were incubated with MBP-Jab1 and MIF; and MIF bound to Malate-beads via MBP-Jab1 is detected with anti-MIF antibodies by Western-Blot, (vii) Protein A-beads were incubated with anti-MIF antibodies and MIF and biotin-Jab1; and streptavidin bound to Protein A beads is detected by Western-Blot, (viii) Protein A-beads were incubated with anti-MIF antibodies and MIF and Jab1; and Jab1 bound to Protein A beads is detected with anti-Jab1 antibodies by western-Blot and (ix) Dynalbeads-streptavidin were incubated with biotin-EGFP-MIF and Jab1; and Jab1 bound to Dynalbeads-streptavidin is detected with anti-Jab1 antibodies by Western-Blot.

The screening for drugs interfering with the MIF/Jab1-interaction can also be done by a protein array, e.g. on a so-called biochip. For instance MIF is immobilised on a solid support, for example a polymeric support or silica wafer or glass slide or nylon membrane, either covalently or non-covalently via e.g. binding of GST-MIF to a solid GSH-support or biotin-MIF to a solid Streptavidin-support or MBP-MIF to a solid malate-support. In accordance with known methods MIF can also be directly immobilised on a solid support via amino acid residues such as Lys or Cys or similar amino acid residues or via non-natural amino acids, whereby no additional tag molecules are needed. The immobilised MIF protein is then incubated with soluble Jab1 in the absence (control) or presence of candidate drugs. The influence of a candidate drug on the interaction between MIF and Jab1 can then be detected by methods such as fluorescence or MALDI-MS detection methods. In another embodiment Jab1 or Jab1-derived domain is immobilised on a solid support either covalently or non-covalently via binding of GST-Jab1 to a GSH-support or biotin-Jab1 to a Streptavidin-support or binding of MBP-Jab1 to a malate-support or direct covalent binding of Jab1 without additional tag molecules via amino acid residues such as Lys or Cys or via non-natural amino acids. The immobilised Jab1 protein is then incubated with soluble MIF in the absence or presence of candidate drugs, whereby the influence of the candidate drugs on the interaction between MIF and Jab1 is detected by fluorescence or MALDI-MS methods.

The materials used in biochips as supports for MIF or Jab1 can comprise any polymeric materials, for example nylon. These polymeric supports can themselves be fixed on a porous mineral support comprising, for example, a metallic oxide such as silica, alumina, magnesia, etc., or natural or synthetic derivatives of these oxide such as glasses, silicates, borosilicates, kaolin etc. The said polymers can be fixed on the porous mineral support by impregnation, the polymer coating then being, if necessary, stabilised by crosslinking in accordance with known methods. The crosslinking agent is, for example, a dicarbonyl compound, a halohydrin, a diepoxide, etc. The polymer supports can also be fixed on mineral supports by means of an intermediate bifunctional coupling agent. The desialyled proteins can also be fixed on the polymeric support by means of an appropriate bifunctional coupling agent, in accordance with known methods. The coupling agents are, for example, bifunctional derivatives such as cyanogen bromide, dialdehydes, diepoxides, etc. The proteins can also be directly fixed on the porous mineral support. For example, in the case of a silica support, an aminoalkylsilane derivative of silica, is prepared and the desialyled protein is fixed on the aminoalkylsilane using a bifunctional agent such as glutaraldehyde; see for example P. J. Robinson et al., Biochem. Biophys. Acta, 242, 659-661 (1971). The desialyled proteins can also be fixed on porous mineral supports in accordance with the method described in French patent application 77.28163 (publication No. 2.403.098). This process comprises coating a porous mineral support with a polymer capable of undergoing a cleavage reaction oxidising the glycol groups using oxidising agents such as periodates. A polycarbonyl coating is obtained and the ligand, for example, the desialyled glycoprotein, can then be fixed on the carbonyl groups formed. If desired, the imine group formed can be reduced to the amine.

In a preferred embodiment, the method for testing the interaction, e.g. binding of MIF and Jab1, is an electromobility shift assay. The MIF-Jab1 binding reduces or enhances the flexibility/mobility of the c-Jun/DNA or Jab1/c-Jun/DNA complexes in a gel (for instance native polyacrylamide gel). Shifts of the DNA probe alone or as part of a complex in the gel in the absence or presence of candidate drugs can be detected by radioactive or fluorescence labelling of the DNA probe.

In accordance with the present invention the method for detecting MIF-Jab1 binding also comprises an array of proteins: MIF-Jab1 protein binding reduces or enhances the flexibility/mobility of MIF and Jab1 in a gel (e.g. native polyacrylamide gel). Shifts of the proteins (MIF, Jab1, MIF-Jab1-complex) in the gel in the absence and presence of candidate drugs can be detected by radioactive or fluorescence labelling of MIF and/or Jab1.

In a preferred embodiment of the present invention, the method for detecting the MIF-Jab1 binding by chromatography also comprises absorbing the MIF in the absence and presence of candidate drugs onto a Jab1-chromatographic support, and washing the column with buffer and detecting the MIF in the eluate or bound MIF directly; e.g. the amount of MIF in the eluate is higher in the presence than in the absence of the candidate drug, if the candidate drug is a dissociator. The method for detecting the MIF-Jab1 binding by chromatography also comprises absorbing the Jab1 in the absence and presence of candidate drugs onto a MIF[-] chromatographic support, [immobilised] *immobilized* anti-MIF-Jab1-domain antibodies and/or [immobilised] *immobilized* anti-MIF-Jab1-fusion protein antibodies etc. and washing the column with buffer and detecting the Jab1 in the eluate; for instance the amount of Jab1 in the eluate is lower in the presence than in the absence of the candidate drug, if the candidate drug is not a dissociator. The method for detecting the MIF-Jab1 binding also comprises adsorbing the soluble MIF [of] *or* Jab in the absence or presence of candidate drugs onto a MTP (microtiter plate) or biochip with immobilised MIF or Jab1.

In a particularly preferred embodiment of the present invention, MIF and/or Jab1 to be used is obtained by in vitro translation.

In another preferred embodiment MIF and Jab1 are contained in crude or partially purified cell extracts. Cell extracts encompassed by the present invention are biological tissue, or liquids or suspensions with cells or fragments thereof. Such cell extracts may be obtained by mechanical agitation or shearing, by sonification, by applying electrical fields, by applying chemical and/or enzymatic agents, etc. to cell or tissues. The present invention also includes any combination of the "in vitro" and "cell extract" methods; e.g. MIF and Jab1 are contained in a suspension, whereby Jab1 is contained in a cell-extract and pure MIF is bound on beads.

In another preferred embodiment, the method for testing the interaction, in particular binding of MIF and Jab1, is an in vivo method. The in vivo method is widely recognised as a particularly reliable measure of the biological activity of the MIF-Jab interaction. Since the in vivo methods of the invention do not involve a potentially toxic metabolism, these methods are particularly useful as a diagnostic tool in measuring interaction of MIF and Jab1 in vivo. In comparison to in vitro methods, the in vivo methods are safe, more widely applicable, more easily performed, more sensitive, produce more accurate results and more reliably to represent the physiological situation. Labelling of MIF and/or Jab1 is accomplished via physiologic substrates rather than potentially toxic, non-physiological metabolites; preservation of the cell and tissue anatomy is not required; and no radioactivity is involved.

The present invention also encompasses with respect to MIF and Jab1 genetically manipulated, in particular transgenic animals, especially mammals, in particular mice and cells thereof. These animals, containing in at least some of their cells for instance, transfected sense or antisense constructs of MIF and Jab1 coding sequences under control of regulatory elements, in particular so called knock-out-animals, are useful for research and diagnosis because the activity of MIF, Jab1 or the MIF-Jab1 interaction is modified. The modification of MIF, Jab1 or of the MIF-Jab1 complex in transgenic animals is possible e.g. by using sense or antisense nucleotide sequences of MIF, Jab1 or MIF-Jab1 fusions, or any modifications of these nucleotide sequences such as inversions, deletions, insertions, additions, etc. to transform and obtain such animals genetically manipulated in both loci, namely MIF and Jab1. Thus, the present invention also relates to animals being genetically modified, in particular being transgenic animals which exhibit a modified MIF and Jab1 expression in contrast to the wildtype animal. Such a modified expression in a mammalian, in particular a non-human mammalian cell may be due to the introduction of MIF and/or Jab1 antisense or sense constructs, possibly containing nucleotide sequence alteration and/or may be due to manipulations in the endogenous nucleotide sequences for the MIF and Jab1 protein. By virtue of these modifications such as insertions of additional mutated or non-mutated sense or antisense copies of MIF and Jab1 or modifications in the endogenous genes, including modifications in the regulatory regions, it is possible to obtain useful animals for the above-identified purposes. The present invention thus also relates to single non-human mammalian cells or cell cultures containing the above identified modifications.

In a preferred embodiment of the present invention the in vivo method comprises a) providing a cell over-expressing MIF and/or Jab1,
b) detecting expression of a MIF-Jab1-complex target activity, in particular the activity of a reporter gene in the absence of a candidate drug,
c) detecting expression of the MIF-Jab1-complex target activity, in particular the activity of a reporter gene in the presence of the candidate drug and
d) comparing the results obtained in b) and c).

In a preferred embodiment of the present invention, the reporter gene is capable of being induced by the MIF-Jab1-complex, e.g. providing binding and effector sites near or at the regulatory sites of the reporter gene and is capable of expressing a gene product coded by the coding region of the reporter gene which, in turn, may be detected directly or indirectly by detection means and methods.

The present invention also relates to a method wherein the cell over-expressing MIF and/or Jab1 is obtained by transfecting a host cell with:

a) a vector comprising a MIF coding sequence under operational control of a promoter,
   a vector comprising a Jab coding sequence under operational control of a promoter,
   a vector comprising the reporter gene or
b) a vector containing the MIF and Jab1 coding gene under the operational control of a single promoter and a vector comprising the reporter gene, or
c) a vector containing MIF and Jab1 coding sequence and the reporter gene under the operational control of the single promoter.

In a particularly preferred embodiment, the promoter is a strong constitutive or inducible promoter such as CMV or Tet. By creating bicistronic or multicistronic constructs which contain MIF, Jab1 and/or reporter genes a coupled expression of MIF, Jab1 and/or reporter genes is allowed. In particular, molecular elements or factors separate genes in a manner that fusion proteins can be prevented.

In a particularly preferred embodiment of the present invention, the reverse two-hybrid-method for determining whether a candidate drug disrupts binding between MIF and Jab1 comprises:

a) providing a cell containing
   i) a reporter gene, operably linked to a DNA binding protein recognition site;
   ii) a first fusion gene expressing a first hybrid protein comprising MIF covalently bonded to a DNA-binding moiety which specifically binds to DNA-binding protein recognition site; and
   iii) a second fusion gene expressing a second hybrid protein comprising Jab1 covalently bonded to a gene activating moiety, wherein Jab1 binds MIF in the absence of drug;
b) contacting the cell with the candidate drug under conditions allowing expression of the reporter gene; and c) detecting inhibition of expression of the reporter gene as a measure of the ability of the candidate drug to disrupt binding between MIF and Jab1.

The invention permits the identification of molecules which dissociate or prevent interaction or binding between MIF and Jab1. The candidate drugs which potentially disrupt binding between MIF and Jab1—the so-called dissociator compounds—can for instance be introduced into cells by simply adding them to cultures. By "dissociator compounds" any molecule is meant which disrupts, prevents or modulates interaction, in particular the binding of MIF and Jab1. Examples of dissociator compounds are polypeptides, nucleic acids, organic and anorganic molecules and ions. Many potential dissociator compounds are small enough that they will be taken up by a cell by endocytosis or diffusion through the membrane, if sufficiently hydrophobic. Alternatively, if the dissociator compound is an RNA molecule or a protein, it can be produced in a cell by transforming the cell with the corresponding DNA construct and expressing the desired RNA or protein. Compounds which stabilise molecular interactions between MIF and Jab1 can also be identified by these methods.

A method for detecting the interaction between MIF and Jab1 is also provided in accordance with the present invention. The method comprises providing a host cell, preferably a procaryotic or eucaryotic cell. The host cell contains a detectable reporter gene having a binding site for a DNA-binding domain of the transcriptional activator, such that the detectable gene expresses a detectable protein when the detectable gene is transcriptionally activated. Such activation occurs when the transcriptional activation domain of a transcriptional activator is brought into sufficient proximity to the DNA-binding domain of the transcriptional activator.

A first chimeric gene is provided which is capable of being expressed in the host cell. A chimeric molecule is a molecule in which two or more molecules that exist separately in their native state are joined together to form a single molecule having the desired functionality of all its constituent molecules. While the chimeric molecule may be prepared by covalently linking two molecules, each of which are synthesised separately, one of skill in the art will appreciate that where the chimeric molecule is a fusion protein, the chimera may be prepared de novo as a single "joined" molecule, i.e. by genetic engineering methods. The first chimeric gene may be present in a chromosome or plasmid of the host cell. The first chimeric gene comprises a DNA sequence that encodes a first hybrid protein. The first hybrid protein contains a DNA-binding domain that recognises the binding side on the reporter gene in the host cell. The first hybrid protein also contains a MIF protein or a MIF protein fragment which is to be tested for interaction with a Jab1 protein or Jab1 protein fragment.

A second chimeric gene is provided which is capable of being expressed in the host cell. In one embodiment, both the first and the second chimeric genes are introduced into the host cell in the form of plasmids. Preferably, however, the first chimeric gene is present in the chromosome of the host cell and the second chimeric gene is introduced into the host cell as part of a plasmid. The second chimeric gene contains a DNA sequence that encodes a second hybrid protein. The second hybrid protein contains a transcriptional activation domain. The second hybrid protein also contains a Jab protein or a Jab protein fragment which is to be tested for interaction with the MIF protein or MIF protein fragment. The DNA-binding domains of the first hybrid protein and the transcriptional activation domain of the second hybrid protein are preferably derived from transcriptional activators having separate DNA-binding and transcriptional activation domains. These separate DNA-binding and transcriptional activation domains are for example known to be found in the yeast GAL4 protein, and are also known to be found in the yeast GCN4 and ADR1 proteins. Numerous other proteins involved in transcription also have separate binding and transcriptional activation domains which make them useful for the present invention. In another embodiment, the DNA-binding domain and the transcriptional activation domain may be from different transcriptional activators. The second hybrid protein may be encoded on the library of plasmids that contain genomic, cDNA or synthetically generated DNA sequences fused to the DNA sequence encoding the transcriptional activation domain.

A variety of DNA-binding moieties and gene activating moieties are suitable for use in the various aspects of the invention. Generally, the DNA-binding domain or gene activating domain of any transcription factor can be used. If desired, the gene activating domain of VP16 can be used. The DNA-binding-protein recognition site and the gene activating and DNA-binding moieties all can correspond to identical transcription factors, or they can correspond to different transcription factors. Useful binding sites include those for the yeast protein GAL4, the bacterial protein LexA, the yeast metal-binding factor Ace1. These binding sites can readily be used with a repressed promoter (e.g. a SPO13 promoter can be used as the basis for SPAL, SPEX and SPACE promoters, respectively, for a SPO13 promoter combined with GAL, LEX and ACE1 DNA binding sites). Other useful transcription factors include the GCN4 protein of S. cerevisiae (see e.g., Hope and Struhol, 1986. Cell 46:885-894) and the ADR1 protein of S. cerevisiae (see, e.g., Kumar et al., 1987, Cell 51:941-951). The DNA-binding protein recognition site should include at least one binding site for the binding domain of the transcription factor that is used. While the number of DNA-binding-protein recognition sites that can be used is unlimited, the number of binding sites is preferably between 1 and 100, more preferably 1 and 20; still more preferably, the number of binding sites is between 1 and 16. The number of binding sites can be adjusted to account for factors such as the desired selectivity or sensitivity of the assay.

The interaction between the MIF protein or parts thereof and the Jab1 protein or parts thereof in the host cell, therefore, causes the transcriptional activation domain to activate transcription of the reporter gene. The method is carried out by introducing the first chimeric gene and the second chimeric gene into the host cell. The host cell is subjected to conditions under which the first hybrid protein and the second hybrid protein are expressed in sufficient quantity for the reporter gene to be activated. The cells are then tested for expression of the reporter gene to a greater degree than in the absence of interaction between the MIF protein and the Jab1 protein.

In a preferred embodiment of the invention, the expression of the reporter gene is determined in host cells subjected to a candidate drug to be screened and compared to the expression of the reporter gene in host cells not subjected to the candidate drug.

In a preferred embodiment the invention relates to a DNA-binding domain and transcriptional activation domain, which are derived from transcriptional activators having separable DNA-binding and transcriptional activation domains.

In a further preferred embodiment of the invention, the DNA-binding domain in the transcriptional activation domain is selected from the group consisting of the transcriptional activators GAL4, GCN4 and ADR1. The system is dependent upon a number of conditions to properly carry out the method of this invention. The interacting MIF protein must not itself carry an activation domain for the marker. The activation domain would otherwise allow transcription of the marker gene as soon as the vector encoding only the GAL4 DNA-binding domain fused to the MIF protein is introduced. The interaction between the MIF protein and the Jab1 protein must be capable of occurring within the yeast nucleus. The GAL4 activation domain portion of the hybrid containing the Jab1 protein must be accessible to the transcription mechanism of the cell to allow transcription of the marker or reporter gene. Should any of these conditions not exist, the system may be modified for use by constructing hybrids that carry only portions of the interacting proteins MIF and Jab1, and thus meet these conditions. Since other eucaryotic cells use a mechanism similar to that of yeast for transcription, other eucaryotic cells can be used instead of yeast to test for the interaction of MIF and Jab1, such as mammalian cells. The reporter gene function can be served by any of a large variety of genes, such as genes encoding resistance or metabolic enzymes or GFP (green-fluorescent protein). The function of GAL4 can be served by any transcriptional activator that has separable domains for DNA-binding and for transcriptional activation. Any protein, including one which is not a transcriptional activator but which has two separable functions, can be used to establish a similar genetic system to detect the MIF-Jab1 interactions.

Accordingly, the method of the present invention can be applied more generally to any detectable function requiring separable domains of an amino acid sequence which can be reconstituted. This general embodiment of the present invention detects interactions between MIF and Jab1. The method includes providing a host cell which is defective in a detectable function. The detectable function is restored/provided by an amino acid sequence having separable domains. Thus, the amino acid sequence includes first and second domains which are capable of producing the detectable function when they are in sufficient proximity to each other within the host cell.

In a particularly preferred embodiment of the present invention, the first hybrid protein and/or the second hybrid protein is encoded on a the library of plasmids containing DNA inserts derived from the group consisting of genomic DNA, cDNA and synthetically generated DNA.

In a further preferred embodiment of the present invention the chimeric genes are introduced into the host cells in the form of plasmids.

In a particularly preferred embodiment of the present invention a first chimeric gene is provided that is capable of being expressed in the host cell. The first chimeric gene includes a DNA sequence that encodes a first hybrid protein. The first hybrid protein contains a first domain of the amino acid sequence. The first hybrid protein also contains a MIF protein or protein fragment which is to be tested for interaction with a Jab1 protein or Jab1 protein fragment.

In another embodiment of the present invention the first chimeric gene is integrated into the chromosomes of the host cell, and the second chimeric gene is introduced into the host cell as part of a plasmid. A second chimeric gene is provided which is capable of being expressed in the host cell. The second chimeric gene contains a DNA sequence that encodes a second hybrid protein. The second hybrid protein contains a second domain of the amino acid sequence. The second hybrid protein also contains a Jab1 protein or fragment which is to be tested for interaction with the MIF protein or the MIF protein fragment. The interaction between the MIF protein and the Jab1 protein in the host cell causes a function of the amino acid sequence to be reconstituted. This is carried out by introducing the first chimeric gene and the second chimeric gene into the host cell. The host cell is subjected to conditions under which the first hybrid protein and the second hybrid protein are expressed in sufficient quantity for the function of the amino acid sequence to be reconstituted. The cells are then tested to determine whether the expression of the function of the amino acid sequence has been reconstituted to a degree greater than in the absence of the interaction of the test substances, e.g. proteins. This generalised method can be made more specific for a preferred method of the present invention in which the detectable function is the transcription of a detectable reporter gene. In this method, the first domain of the amino acid sequence includes a DNA-binding domain that recognises a binding site on the detectable reporter gene, and the second domain of the amino acid sequence includes a transcriptional activation domain.

In a particularly preferred embodiment of the present invention, the DNA-binding domain and the transcriptional activation domain are from different transcriptional activators.

The present invention also relates to a method of preparing a MIF protein comprising: (i) providing a source containing the MIF protein, (ii) contacting the source containing the MIF protein with a source containing the Jab1 under conditions allowing for both the (iii) binding of MIF and Jab1 and the (iv) separation of MIF from Jab1.

The method for purifying MIF from a source for example comprises:

a) concentrating the source of MIF;
b) absorbing the MIF onto a Jab1-chromatographic support;
c) washing the absorbed MIF with at least one buffer;
d) selectively eluting the washed MIF, and
e) recovering the MIF from the eluate.

Additionally, the method for purifying could be used for:

(i) purifying recombinant MIF from bacteria,
(ii) purifying native MIF from tissue,
(iii) purifying MIF-like homologues such as certain tautomerases,
(iv) purifying "native" MIF without harsh treatment whereby Jab1 is used as a soft capter molecule.

This technique makes use of the fact that MIF and Jab1 interact in a specific way. This affinity chromatography relies on the interaction of the MIF protein with an immobilised ligand (e.g. Jab1). The ligand of the invention can be specific for the particular protein of interest, in which case the ligand is a substrate, substrate analogue, inhibitor or antibody which reacts with MIF. In order to isolate MIF from a source such as a cell extract, a sample of the cell extract is for instance placed on a column composed of Jab1-functionalised or coated polymers, and the column is washed repeatedly with buffer. The only proteins that are retained on the column are those with a high affinity to the Jab1 anchored to the polymer; other proteins are simply washed out. To elute MIF fixed on the affinity chromatography support of the present invention, a buffer solution containing, at a sufficient concentration, salts and/or known chaotropic agents, such as magnesium chloride or a carbonate buffer may be employed, e.g. since the affinity and specificity between MIF and Jab1 is very high, MIF or Jab1 can isolated and purified from a cell extract. This chromatography improves the existing method of preparing MIF and it provides a method for preparing Jab1.

The polymers used as supports for Jab1 can themselves be fixed on a porous mineral support comprising, for example, a metallic oxide such as silica, alumina, magnesia, etc., or natural or synthetic derivatives of these oxide such as glasses, silicates, borosilicates, kaolin etc. The said polymers can be fixed on the porous mineral support by impregnation, the polymer coating then being, if necessary, stabilised by crosslinking in accordance with known methods. The crosslinking agent is, for example, a dicarbonyl compound, a halohydrin, a diepoxide, etc. The polymer supports can also be fixed on mineral supports by means of an intermediate bifunctional coupling agent. The desialyled proteins can also be fixed on the polymeric support by means of an appropriate bifunctional coupling agent, in accordance with known methods. The coupling agents are, for example, bifunctional derivatives such as cyanogen bromide, dialdehydes, diepoxides, etc. The proteins can also be directly fixed on the porous mineral support. For example, in the case of a silica support, an aminoalkyl-silane derivative of silica, is prepared and the desialyled protein is fixed on the aminoalkylsilane using a bifunctional agent such as glutaraldehyde; see for example P. J. Robinson et al., Biochem. Bio-phys. Acta, 242, 659-661 (1971) The desialyled proteins can also be fixed on porous mineral supports in accordance with the method described in French patent application 77.28163 (publication No. 2.403.098). This process comprises coating a porous mineral support with a polymer capable of undergoing a cleavage reaction oxidising the glycol groups using oxidising agents such as periodates. A polycarbonyl coating is obtained and the ligand, for example, the desialyled glycoprotein, can then be fixed on the carbonyl groups formed. If desired, the imine group formed can be reduced to the amine.

Thus, the present invention relates to a method of preparing the Jab1 protein comprising:

a) providing a source containing the Jab1 protein, b) contacting the source containing the Jab1 protein with the source containing the MIF protein under conditions following the binding of Jab1 and MIF and separating Jab1, the isolated peptides, proteins or fragments can be purified by biochemical methods including, for example, affinity chromatography. Affinity matrices which can be used for MIF or Jab1 (e.g. human MIF peptides) isolation can be anti-MIF monoclonal or polyclonal antibodies prepared against the amino acid sequence coding MIF or Jab1, or fragments thereof such as synthetic peptides, recombinant fragments or the like. Alternatively, cognate binding domains or polypeptides as well as other compounds known in the art which specifically bind to MIF can similarly be used as affinity matrices to isolate substantially proteins or antibodies (e.g. pure human MIF proteins, semi-pure mice Jab1 polypeptides or antibodies which interact with the MIF-Jab1 domain) of the invention. The chromatography provides an isolating method for yet unknown Jab1 homologues—such as proteins of the MOV34 family or proteins with a MPN domain like Pad1—by binding homologous domains to MIF.

In a preferred embodiment of the present invention, the sources containing MIF and/or Jab1 are cells including bacteria or yeast or recombinantly prepared cells, tissues, cell cultures, cell culture supernatants, cell extracts, protein preparations, isolated MIF or Jab1.

In a particularly preferred embodiment of the present invention, the source containing the MIF protein is pretreated, in particular disrupted, prior to contacting MIF and Jab1, if necessary, for instance, cells used as a source may be sonificated, chemically or enzymatically lysed or subjected to pulsed or constant electrical fields.

The present invention also relates to a, preferably isolated and purified, complex protein comprising all or part of the MIF protein in not covalently bonded association with all or part of the Jab1 protein. The complex of MIF and Jab1 relates to naturally occurring or wildtype complex as well as to any modification, mutants or derivatives such as recombinantly produced complexes containing amino acid modifications, such as inversion, deletions, insertions, substitutions, additions, denaturations, oxidations of each of the two components of the complex, i.e. of either MIF or Jab1 or both etc.

Thus, the present invention also relates to a, preferably isolated and purified fusion protein comprising all or part of the MIF protein covalently bonded in conjunction with all or part of Jab protein. The fusion protein relates to naturally occurring or wildtype fusion proteins as well as to any modification, mutants or derivatives such as recombinantly produced fusion proteins containing amino acid modifications, such as inversions, deletions, insertions, substitutions, additions, denaturations, oxidations of each of the two components of the complex, i.e. of either MIF or Jab1 or both etc.

The present invention also relates to a purified and isolated nucleic acid sequence encoding the fusion protein according to the above, or the complementary strand thereof. The term nucleic acid sequence relates to a natural or synthetic polymer of DNA or RNA which may be single or double stranded, alternately containing a synthetic, non-natural or altered nucleotide base capable of incorporation into DNA or RNA polymers. The nucleic acid molecule may be cDNA, genomic DNA, or RNA, for instance mRNA.

The present invention also relates to a vector comprising the nucleic acid sequence according to the above, in particular to a bacterial vector, such as a plasmid, a liposome, a bacteriophage, a retrovirus or a virus.

Furthermore, the present invention relates to host cells transformed with a vector of the present invention, in particular procaryotic or eucaryotic cells. The present invention also relates to cell cultures, tissues, etc. comprising a cell containing a plasmid according to the above.

The present invention also relates to an antibody or fragment thereof which is specifically reactive with the complex of MIF and Jab1 or the fusion protein of MIF and Jab1 or the interacting domain of MIF and Jab1. These antibodies may be used to screen expression libraries to identify clones which produce the complexes of the present invention and also for therapeutic purposes. As used herein, the term "relates to an antibody" relates to detection, activation or inhibition of molecular and cellular pathways induced by the interaction of Jab1 and MIF. The term "antibody" relates to bivalent and monovalent molecular entities that have the property of interaction with a complex of MIF and Jab1. As used herein, "antibody" refers to a protein consisting of one or more polypeptides substantially encoded by immunoglobulin genes or fragments of immunoglobulin genes. Light chains are classified as either kappa or lambda. Heavy chains are classified as gamma, mu, alpha, delta, or epsilon, which in turn define the immunoglobulin classes, IgG, IgM, IgA, IgD and IgE, respectively (for details see definition of the terms). The phrase "specifically binds to", when referring to an antibody, refers to a recognition and binding reaction which is determinative of the presence of the domain in question in the presence of a heterogeneous population of proteins and other biologics. Thus, under designated immunoassay conditions, the specified antibodies bind to the particular domain and do not bind in a significant amount to other proteins present in the sample. Specific binding to the domain under such conditions may require an antibody that is selected for its specificity for a MIF-Jab-domain. A variety of immunoassay formats may be used to select antibodies specifically immunoreactive with the MIF-Jab1-domain. For exammple, solid phase ELISA immunoassays are routinely used to select monoclonal antibodies specifically immunoreactive with the domain. The immunoassays which can be used include, but are not limited to, competitive and non-competitive assay systems using techniques such as Western-Blots, radioimmunoassays, immunoprecipitation assays, precipitin reactions, gel diffusion precipitin reactions, immunodiffusion assays, agglutination assays, complementfixation assays, immunoradiometric assays, fluorescent immunoassays and protein A inununoassays, to name but a few. Antibodies of the invention specifically bind to one or more epitopes on a domain which is involved in the interaction of MIF and Jab1. Epitope refers to the region of a MIF-Jab1-complex or of the MIF-Jab1 interacting domain or of the MIF-Jab1 fusion protein bound by an antibody, wherein the binding prevents association of a second antibody to an MIF-Jab1-complex, or wherein the antibody prevents binding of other proteins (upstream kinases, c-Jun, JNK, SRC-1, LFA-1, PR, GR, etc.).

In an embodiment of the invention, the antibodies are polyclonal antibodies, monoclonal antibodies and fragments thereof. Antibody fragments encompass those fragments which interact with an MIF-Jab1-complex. Also encompassed are humanised antibodies, typically produced by recombinant methods, wherein human sequences comprise part or all of an antibody which interacts with a MIF-Jab1-complex. Examples of humanised antibodies include chimeric or CDR-grafted antibodies. Also included are fully human antibodies of the MIF-Jab1-complex produced in genetically altered mice. Antibodies of the invention may also have a detectable label attached thereto. Such a label may be a fluorescent (e.g. fluorescein isothiocyanate, FITC), enzymatic (e.g. horse radish oxidase), affinity (e.g. biotin), or isotopic label (e.g. $^{125}$I).

Also encompassed by the invention are hybridoma cell lines producing a monoclonal antibody which interacts with a MIF-Jab1-complex.

The antibodies of the present invention are useful in diagnosing MIF related diseases. Antibodies may be used as part of a diagnostic kit to detect the presence of the interaction of MIF and Jab1 in a biological sample. The biological samples include tissues, specimens and intact cells or extracts thereof. Such kits employ antibodies having an attached label to allow for detection. The antibodies are useful for identifying normal domains of the interaction of MIF and Jab1; the antibodies of the invention are also useful for diagnosing and therapy.

The present invention also relates to a kit comprising nucleic acid sequence which encodes the fusion protein of the invention, the vector comprising said nucleic acid sequence, the host cell comprising said vector, the DNA sequence encoding MIF and/or Jab1, the complex or fusion molecule comprising MIF and/or Jab1 and the antibodies of the invention. In the context of the invention, the MIF-Jab1 complex can be contained in liposomes with a pure lipid or biological membrane. The DNA which encodes MIF-Jab complex can be used as adjuvant or as a substance for immunisation. The liposomes or the adjuvant are useful for diagnosis and therapy of MIF- and/or Jab1-related diseases.

The method of the present invention as described above may be practised using a kit for detecting the interaction between a MIF and a Jab1. The kit includes a container, two vectors and a host cell. The first vector contains a promoter and may include a transcription termination signal functionally associated with the first chimeric gene in order to direct the transcription of the first chimeric gene. The first chimeric gene includes a DNA sequence that encodes a DNA-binding domain and unique restriction sites for inserting a DNA sequence encoding a protein with an activity of MIF or a protein fragment of the activity of MIF in such a manner that the MIF is expressed as part of a hybrid protein with a DNA-binding domain. The first vector also includes a means for replicating itself in the host cell and in bacteria. Also included on the first vector is a first marker gene, the expression of which in the host cell permits selection of cells containing the first marker gene from cells that do not contain the first marker gene; the first vector is preferably a plasmid. All the above identified methods to detect interaction between MIF and Jab1, in particular to screen for a drug, are carried out under conventional conditions, binding assays for instance in aqueous medium under conditions suitable to detect binding of MIF to Jab1.

The kit also includes a second vector which contains a second chimeric gene. The second chimeric gene also includes a promoter and a transcription termination signal to direct transcription. The second chimeric gene also includes a DNA sequence, certain coded transcriptional activation domains and a unique restriction site to insert a DNA sequence encoding the protein or protein fragment with the activity of Jab1 into the vector in such a manner that the Jab1 or the protein or protein fragment with the Jab1 activity is capable of being expressed as a part of a hybrid protein with a transcriptional activation domain. The DNA binding domain of the first hybrid protein and the transcriptional activation domain of the second hybrid protein are preferably derived from transcriptional activators having separate DNA binding and transcriptional activation domains. The separate DNA binding and transcriptional activation domains are also known to be found in the yeast GAL4 protein and are also known to be found in the yeast GCN4 and ADR1 proteins. Many other proteins involved in transcription also have separable binding and transcriptional activation domains which render them useful for the present invention. In another embodiment, the DNA-binding domain in the transcriptional activation domain may be from different transcriptional activators. The second hybrid protein may be encoded on the library of plasmids that contain genomic, cDNA or synthetically generated DNA sequences fused to the DNA sequence encoding the transcriptional activation domain. The second vector further includes a means for replicating itself in the host cell and in bacteria. The second vector also includes a second marker gene, expression of which in the host cell permits selection of cells containing the second marker gene from cells that do not contain the second marker gene. The kit includes a host cell which contains the detectable reporter gene having a binding site for a DNA-binding domain of the first hybrid protein. The binding site is positioned so that the reporter gene expresses a detectable protein when the detectable reporter gene is activated by the transcriptional activation domain encoded by the second vector. Activation of the detectable gene is possible if the transcriptional activation domain is in sufficient proximity to the reporter gene. The host cell itself is incapable of expressing a protein having a function of the first marker gene, the second marker gene, the DNA-binding domain or the transcriptional activation domain. Accordingly, through use of the kit, the interaction of MIF and Jab1 in the host cell causes a measurably greater expression of the reporter gene than is the case when the DNA-binding domains in the transcriptional activation domain are present, in the absence of interaction between the MIF and the Jab1 protein. The reporter gene may encode an enzyme or other products that can be readily measured. The cells containing the two hybrid proteins are incubated in a appropriate medium and the culture is monitored for the measurable activity. A positive test for this activity is an indication that the MIF and the Jab1 protein have interacted. Such interaction brings their respective DNA-binding and transcriptional activation domains into sufficiently close proximity to cause transcription of the marker gene.

The present invention also relates to protein array kits for detecting the influence of candidate drugs on the interaction between MIF and Jab1. One kit comprises in a container a biochip, wherein MIF is directly immobilised on a solid support, a biochip, wherein Jab1 is directly immobilised on a solid support, a MIF protein or peptide in lyophilised form, a Jab1 protein or peptide in lyophilised form and a buffer system. Another kit comprises two biochips, wherein each of MIF and Jab1 is immobilised as a GST-protein on a GSH-support, lyophilised MIF, lyophilised Jab1 and a buffer system. Another kit comprises two biochips, wherein each of MIF and Jab1 is immobilised as a biotin-protein on a Streptavidin-support, lyophilised MIF, lyophilised Jab1 and a buffer system. Another kit comprises two biochips, wherein each of MIF and Jab1 is immobilised as a MBP-protein on a malate-support, lyophilised MIF, lyophilised Jab1 and a buffer system. The different kits for screening potential drugs are used as follows. The lyophilised MIF protein or peptide is dissolved in the buffer and is then brought into contact with the biochip comprising the immobilised Jab1 in the presence or absence of a potential drug. For comparison the lyophilised Jab1 peptide or protein is also dissolved in the buffer and brought into contact with the biochip comprising the immobilised MIF in the presence or absence of a potential drug. Then the above described methods to detect the interaction between MIF and Jab1, in particular fluorescence or MALDI-MS methods are conducted under conventional conditions.

The present invention also relates to a pharmaceutical or diagnostic composition comprising the nucleic acid sequence of the invention, the vector comprising this nucleic acid sequence, the host cell which comprises the vector of the invention, the DNA sequence encoding Jab1 and/or MIF, the antibodies of the invention and/or the complex or fusion molecules which comprise MIF and Jab1, optionally in conjunction with a pharmaceutically acceptable carrier and/or further additives such as flavouring agents, binders, sweeteners, fillers, bulking agents, pharmaceutically acceptable salts, anorganic or organic acids, preservatives, emulgators etc.

The present invention also relates to the use of Jab1 or a Jab1 coding nucleotide sequence to modulate the activity of MIP, in particular for treatment of MIF-related diseases.

Thus, the present invention also relates to the use of Jab1 or a Jab1 coding nucleotide sequence for preparing a medicament, drug or therapeutic agent for the treatment of MIF-related diseases.

Furthermore, the present invention relates to the use of Jab1 or a Jab1 coding nucleotide sequence for the detection of MIF-related diseases.

The present invention relates to the use of the complex protein and/or the fusion protein for preparing a drug for the diagnosis and/or treatment of MIF-related diseases.

Furthermore, the present invention relates to the use of the complex protein and/or the fusion protein for the diagnosis and/or treatment of MIF-related diseases.

The present invention also relates to the use of the antibodies or a fragment thereof recognising specifically the complex and/or the fusion protein comprising all or part of MIF in association with all or part of Jab1 or an antibody recognising Jab1 or a fragment thereof for preparing a drug for the diagnosis and/or treatment of MIF-related diseases.

The present invention also relates to the use of the antibody of the invention or an antibody to Jab1 or a fragment thereof for the diagnosis and/or treatment of MIF-related diseases.

Furthermore, the present invention relates to a drug comprising Jab1 or a part thereof for a Jab1 coding nucleotide sequence or an antibody specifically recognising Jab1 in a pharmaceutically effective amount.

The present invention relates to the use of the MIF or a MIF coding nucleotide sequence to modulate the activity of Jab1, in particular for treatment of Jab1-related diseases. Jab1-related diseases refers to inflammatory and/or anti-inflammatory effects, the regulation of immunomodulated pathways, septic shock, physiological stress, diseases in connection with cytokine activity, cytokine dependent signalling pathways, cell cycle dependent diseases, skin diseases such as UV-induced skin disorders, abnormal cell growth diseases and cancer and inflammatory processes.

The present invention relates also to the use of MIF or the MIF coding nucleotide sequence for preparing a drug for the diagnosis and/or treatment of Jab1-related diseases.

Thus, the present invention also relates to a process for modifying Jab1 activity in vivo or in vitro, in particular for diagnosing or treating a Jab1 related disease, whereby MIF, part of MIF, a MIF antibody, a MIF nucleotide sequence, such as a DNA or mRNA, possibly cloned for instance in sense or antisense orientation to appropriate regulatory elements in a vector is used to modulate and/or regulate Jab1 activity and/or expression thereof by e.g. modifying transcription, degradation of Kip, binding of c-Jun and/or modifying the cell cycle etc.

Furthermore, the present invention relates to the use of MIF or the MIF coding nucleotide sequence for the diagnosis and/or treatment of Jab1-related diseases.

Thus, the present invention relates to the use of the complex protein comprising all or part of MIF in association with all or part of Jab1, optionally in association with Kip and/or c-Jun or JunD and/or JNK and/or SRC-1 and/or LFA-1 and/or PR and/or GR, and/or the fusion protein comprising all or part of MIF in conjunction with all or part of Jab1, optionally in conjunction with Kip and/or c-Jun or JunD for preparing a drug for diagnosis and/or treatment of Jab1-related diseases.

The present invention relates also to the use of the complex protein of the invention and/or the fusion protein of the invention for diagnosis and/or treatment of Jab1-related diseases.

The present invention relates to use of the [anti-body] *antibody* or a fragment thereof recognising specifically the complex or the fusion protein of the present invention or an antibody to MIF or a fragment thereof for preparing a drug for the diagnosis and/or treatment of Jab1-related diseases.

The present invention also relates to the use of the antibody or a fragment thereof recognising specifically the complex and/or the fusion protein of the present invention or an antibody to MIF or a fragment thereof for the diagnosis and/or the treatment of Jab1-related diseases.

Furthermore, the present invention relates to a drug comprising MIF or a part thereof or a MIF coding nucleotide sequence or an antibody specifically recognising MIF in a pharmaceutically effective amount.

Further preferred embodiments are exemplified in the subclaims.

Figure 1:
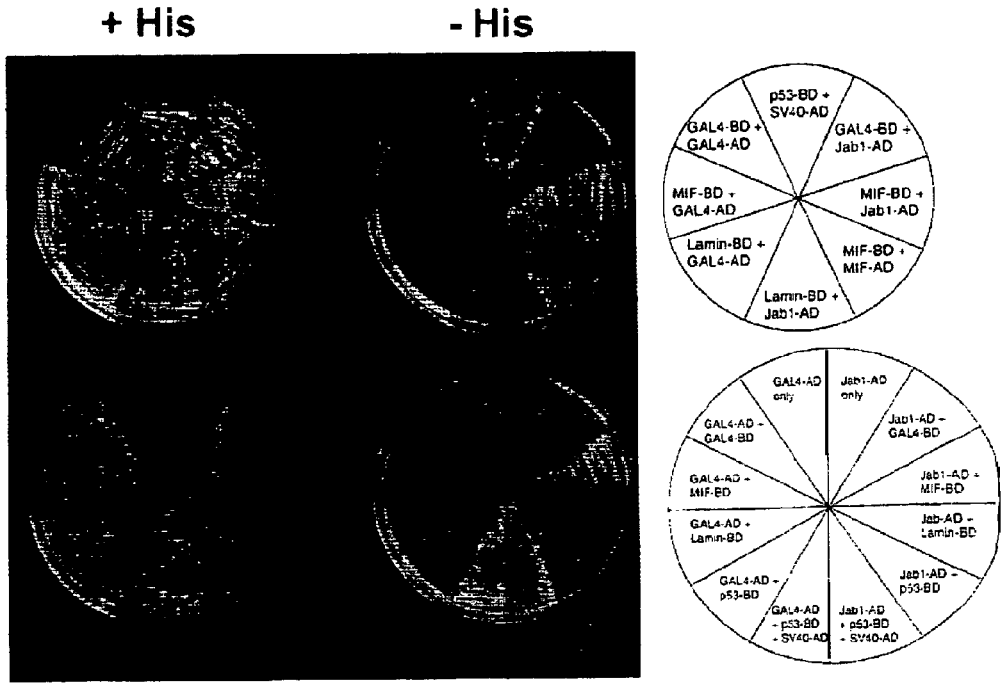
FIG. 1 shows interaction of MIF with Jab1.
Figure 1:
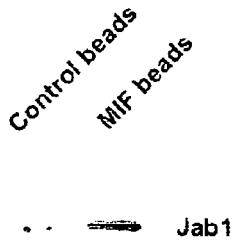
Figure 1:
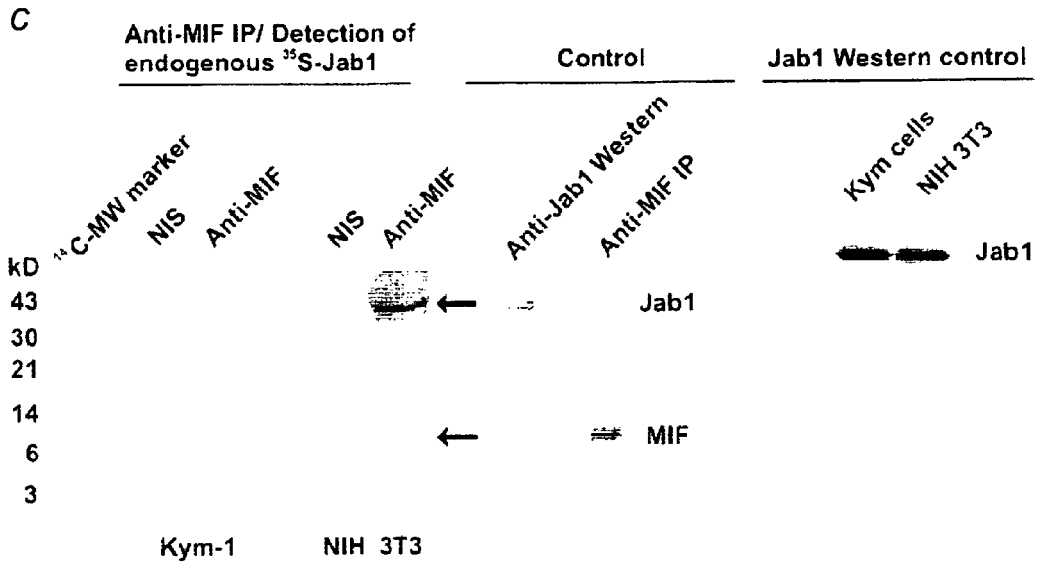

SEQ ID No. 1 depicts the amino acid sequence of MIF (50-65).

SEQ ID No. 2 depicts the amino acid sequence of $Ser^{57}$ $Ser^{60}$ MIF (50-65).

The following examples are offered to more fully illustrate the invention, but are not construed as limiting the scope thereof.

EXAMPLE 1

Detecting interaction of MIF with Jab1 using the two hybrid system.

Materials and Methods used throughout the examples

Recombinant proteins, fusion constructs, and antibodies

Recombinant human MIF was purified from E. coli as described in Kleemann et al., Eur. J. Biochem 261, 753 (1999). For [35S]-radiolabelling, human MIF was expressed in E. coli BL21(DE3) grown in standard minimal medium supplemented with PRO-MIX (Amersham) and purified as described for rMIF in Bernhagen, Biochemistry 33, 14144 (1994). The complete coding sequence of Jab1 was obtained by RT-PCR from Jurkat cells and confirmed by bidirectional sequencing. The Jab1 cDNA was cloned into the pCl-neo vector (Promega) for expression in the in vitro translation and transfection experiments. TNF was from R&D Systems. EGFP fusion proteins: EGFP was C-terminally fused to MIF using the pN3-EGFP vector (Clontech). P33-EGFP as a mitochondrial marker has been described. PKCP(KD)-EGFP shows cytosolic localisation, and was used as the respective control. Rabbit polyclonal anti-rMIF antibody was obtained as described in Bernhagen et al., Nature 365, 756 (1993). All other antibodies were from Santa Cruz Biotechnology.

In Vitro Transcription/Translation Reaction

Coupled in vitro transcription/translation reactions were performed with the TNT T7 Quick reticulocyte-lysate system in combination with the Transcend non-radioactive translation detection system (Promega). Expression of Jab1 and c-Jun was achieved using plasmids pCl-neo-Jab1 (see above) and pBAT-c-Jun. Expression efficiency of biotin-labelled Jab1 and c-Jun was confirmed by immunoblotting using anti-Jab1 or anti-c-Jun anti-body, respectively, or by staining with streptavidin/horse radish peroxidase conjugate (S—HRP).

Protein-Protein Interaction

Immobilisation of rMIF was performed on Affigel 10 agarose (BIO-RAD) at pH 8.5 following the manufacturer's recommendations. Control beads were blocked with L-glycine, pH 8, and bovine serum albumin (BSA). Binding of Jab1 to beads was analysed in lysates from 293T cells that had been transiently transfected with pCl-neo-Jab1 for 48 h (efficiency>80%). Cell lysis (30 min on ice) was done in 25 mM HEPES, pH 7.7, 0.4 NaCl, 1.5 mM $MgCl_2$, 2 mM EDTA, 0.5% Triton X-100, 3 mM DTT, and 1×proteinase inhibitor cocktail (PI) (Roche Diagnostics). Binding and washes were performed in the same buffer, except that NaCl was diluted to 0.1 M. For binding of soluble rMIF to Jab1, TNT reticulocyte lysates were supplemented with 1 μM rMIF of BSA, biotin-labelled Jab1 or c-Jun expressed by in vitro transcription/translation, reactions diluted sixfold in phosphate-buffered saline (PBS) containing PI, and reactions rotated at 4° C. for 3 h. Antibody was added, reactions incubated for 1 h, and immunoprecipitates bound to protein A-Sepharose (Amersham-Pharmacia)(1 h, 4° C.), washed in PBS, and then 50 mM Tris-HCl, pH 8.0, 170 mM NaCl, 0.5% NP-40, 50 mM NaF. Coimmunoprecipitated biotinylated proteins were detected by immunoblotting and S—HRP staining. For co-precipitation of biotinylated MIF-EGFP with Jab1, strepavidin-conjugated magnetic beads (Dynal) were used, complexes washed as above, and Jab1 detected with anti-Jab1 antibody following immunoblotting.

For binding of soluble rMIF to in vitro-synthesised Jab1, TNT lysates were depleted of endogenous MIF (estimated at 10 nM) by incubation of lysates in ELISA plates coated with anti-MIF antibodies (100 μg/well) for 1 h at 4° C. Lysates were supplemented with 1 μM rMIF, control buffer, or bovine serum albumin (BSA), and biotin-labelled Jab1 or c-Jun expressed. Reactions were diluted 6-fold in phosphate-buffered saline (PBS) containing proteinase inhibitor cocktail (PI) (Roche), and rotated at 4° C. for 3 h. Complexes were immunoprecipitated by antibody/protein A-Sepharose (Amersham-Pharmacia) (1 h each, 4° C.), washed in PBS, and then 50 mM Tris-HCI, pH 8.0, 170 mM NaCl, 0.5% NP-40, 50 mM NaF. Coimmunoprecipitated biotinylated proteins were detected by immunoblotting and S—HRP staining.

Interaction of endogenous MIF with endogenous Jab1 was analysed in lysates of untreated 293T cells. MIF/Jab1 complexes were precipitated with anti-Jab1 in comparison to control antibody or protein A-Sepharose alone and immunoblots analysed with anti-MIF antibody.

Tissue Culture and Transient Transfections

Cell lines were cultured according to the recommended standard procedures. All transient transfections were performed using Superfect (Qiagen). For coincubations with Rmif, mif was added 2 h after addition of plasmids. Transfections of serum-starved NIH3T3 cells were performed as reported (Tomoda et al. 1999).

Raw cells expressing reduced amounts of endogenous MIF protein were obtained by transfecting cells with the pBK/antisense MIF expression vector (Waeber et al., 1997). Control cells were transfected with an empty pBK plasmid. Stably transfected clones were isolated. One clone, ΔAS 2.23, expressing <50% of MIF content of control cells, was used.

Raw or HeLa cells were incubated with [35S]rMIF, FLUOS-MIF, biotin-MIF (1 μM each), or labelling reagents alone for 1 h, cells washed in ice-cold PBS and 50 mM glycine, 150 mM NaCl, pH 3, and prepared for liquid scintillation counting, fluorescent microscopy, or confocal microscopy by standard procedures. For [35S]rMIF experiments, cells were subjected to subcellular fractionation by differential centrifugation and cytosolic fractions analysed by PD10 gel filtration. For colocalisation studies, HeLa cells were transfected (1 μg pMIF-EGFP) and cells incubated for to 24 h. Cells were washed, fixed permeabilised with 0.05. Tween-20, and blocked with 5% goat serum. For Jab1 staining, anti-Jab1 antibody and Alexa-546 staining was used. Samples were analysed with a confocal laser scanning microscope (Leica) using filters for Alexa-546, GFP, and FLUOS emissions.

Activity Assays

AP-1 reporter gene activity was measured as reported (Johannes et al., 1998). 0.15 μg of pCl-neo-Jab1 or empty plasmid and 0.05 μg of each the Tk-LUC-5×12-o-tetradecanol phorbol acetate (TRE) (Angel et al., 1987), R15—RSV-LacZ reporter constructs, and the pEGFP plasmid were used. Incubations with rMIF were performed for 18 h. NFκB reporter gene activity measurements in 293T cells were performed as described (Johannes et al., 1998), with rMIF added for 40 h. The NFκB assay in Raw cells was performed as described (Roger et al., 1998). JNK assays were performed as described (Berberich et al., 1996), with rMIF added for 48 h. $p27^{Kpi1}$ induction experiments and proliferation studies were performed following a published procedure (Tomoda et al., 1999). For pulse-chase labelling of $p27^{KiP1}$, a previous method (Tomoda et al., 1999) was adapted, with synchronised fibroblasts plated at $7\times10^5$ cells/well, and 1 μM rMIF added at plating, the pulse, and for the chase period.

RESULTS

Interaction of MIF with Jab1

In order to test the possibility that MIF has direct intracellular functions by interacting with intracellular proteins, the two-hybrid screen was used. The entire coding region of human MIF was fused in-frame to the GAL4 DNA-binding domain using the pAS2-1 vector. With the resulting bait plasmid PMIF-BD, a human fetal brain library was screened by the yeast two-hybrid method essentially as described by the manufacturer (Clontech). Although MIF oligomerises, autoactivation by MIF was not detected. Following selection on Trp-Leu-His-medium and testing the resultant clones for β-galactosidase activity, three positive GAL4 DNA-activation domain fusion proteins were obtained. The results of the β-galactosidase assay in liquid media are in Miller units and are the means±SD of 7 measurements from independent clones.

As MIF is abundantly expressed in the brain and in lymphocytes, a human whole brain and a lymphocyte cDNA library were employed and full-length human MIF cDNA was used as a bait. From $3.5\times10^6$ and $3.0\times10^6$ transfectants, respectively, a total of 4 types of clones that interacted specifically when tested for nutritional selection and β-galactosidase activity was identified. One such clone contained a cDNA insert, with almost the entire coding sequence (corresponding to amino acids 20-335) of human $p38^{Jab1}$. (identity: >99% to the corresponding $p38^{Jab1}$. sequence). The entire coding sequence of 2 other clones was 100% identical to the human MIF cDNA sequence, confirming that MIF self-associates into oligomeres. It is concluded that MIF specifically binds to Jab1 in the yeast two-hybrid assay.

FIG. 1 shows interaction of MIF with Jab1. a, MIF specifically binds to Jab1 in the yeast two-hybrid assay. Growth of transformants coexpressing MIF and Jab1 on selective medium. MIF-BD corresponds to the Ga14-BD/MIF fusion construct; Jab1-AD and MIF-AD represent the clones obtained from the screening. Lamin-BD, Ga14-BD, and Ga14-AD were negative and p53-BD and SV40-AD positive controls. Upper panel, transformation of BD clones first; lower panel, transformation of AD clones first. Leu+ Trp+ transformants were streaked on media lacking leucine and tryptophan (+His) or leucine, tryptophan, and histidine (−His). When quantitated by a liquid media assay, beta-galactosidase activity of the Jab1-AD/MIF-BD sample was found to have 2.1±0.2 beta-galactosidase (β-Gal) units as compared to 0.1±0.1 units for GAL4-AD/GAL4-BD, 0.1±0.04 units for GAL4-AD/MIF-BD, and 0.3±0.1 units for JAB1-AD/GAL4-BD. The SV40-AD/p53-BD positive control had 99±25 units. The results of the beta-galactosidase assay in liquid media are in Miller units and are the mean SD of 7 measurements from independent clones. b, Immobilised MIF specifically interacts with Jab1. MIF immobilised on streptavidin beads was incubated with Jab1 overexpressed in 293T cells, complexes isolated by pulldown, and bound Jab1 detected by immunoblotting with anti-Jab1 antibody/HRP-ECL staining. c, Interaction of endogenous MIF with endogenous Jab1 in vivo. Metabolic labelling of MIF-positive versus MIF-negative cells and pull-down of endogenous MIF/Jab1 complexes by anti-MIF antibody. Left panel, MIF-positive NIH 3T3 fibroblasts versus MIF-negative Kym-1 cells were labelled with [$^{35}$S] cysteine/methionine, MIF-containing complexes immunoprecipitated with anti-MIF versus non-immune antibody, and bound radioactive proteins electrophoresed. 14 C-radiolabelled molecular weight marker was co-electrophoresed. Fibroblasts ($1\times10^6$ cell equivalents) were MIF-positive by Western blotting (scored 3 on a scale of 0-3) and were determined to contain >300 fg MIF/cell by ELISA. Kym-1 cells were MIF-negative by Western blotting (score of 0) and contained 7±5 fg MIF/cell (mean±SD; n=3) as measured by ELISA. Right panel, anti-Jab1 and anti-MIF control Western blots. Anti-Jab1 Western blot in the lower panel demonstrates that Kym-1 and NIH 3T3 cells contain approximately equal concentrations of endogenous Jab1. For this Western analysis, 5×10 5 cell equivalents were electrophoresed for each cell type. Staining was performed with anti-Jab1 antibody/HRP-ECL chemiluminescence.

EXAMPLE 2

Detecting Interaction of MIF with Jab Using Co-Precipitation

The specificity of the interaction between MIF and $p38^{Jab1}$ was probed by in vitro co-precipitation experiments. Purified recombinant human MIF (rMIF) was immobilised on agarose beads, and binding to full length $p38^{Jab1}$ that was cloned from Jurkat T cells and overexpressed in 293 human embryonal kidney cell was assessed. $p38^{Jab1}$ strongly bound to the MIF beads, whereas only non-specific background binding was observed to non-functionalised control beads. Furthermore, soluble rMIF could specifically bind to in vitro-translated biotin-labelled $p38^{Jab1}$, whereas biotin-labelled c-Jun was not co-precipitated by MIF. Reversely, biotin-labelled MIF-enhanced green fluorescent protein (MIF-EGFP) fusion protein bound to $p38^{Jab1}$.

Significant portions of $p38^{Jab1}$ are found in the nucleus and cytosol, suggesting that interaction with MIF would occur in one of these compartments. Staining of endogenous MIF with anti-MIF antibody and Cy-2 and transient transfection of a MIF-EGFP fusion protein in HeLa and COS-1 cells and microscopic comparison of the subcellular localisation with other EGFP-linked marker proteins revealed that both endogenous MIF and overexpressed MIF fusion protein predominantly located to the cytosol. As circulating extracellular MIF is critical for the numerous immunological functions of MIF, it was also tested whether extracellular MIF may be targeted to the cytosol. Exogenously added [$^{35}$S]rMIF, in addition to being recoverable from the lysosome fraction, was targeted to the cytosol in significant concentrations and was stable there for several hours, indicating that transcellularly acting MIF could interact with $p38^{Jab1}$ following uptake into target cells.

Specific complex formation between MIF and Jab1 in vitro was also observed when both proteins were expressed in the in vitro translation system. It is demonstrated that complexes of biotin-labelled MIF-enhanced green fluorescent protein (MIF-EGFP) fusion protein and non-biotinylated Jab1 were specifically precipitated. Furthermore, biotinylated rMIF, when added to Raw 264.7 macrophages or HeLa cells, bound to endogenous Jab1 in vivo. This latter finding also demonstrates that MIF added exogenously to cells can bind to endogenous intracellular Jab1 following endocytosis.

Finally, in vivo interaction of the endogenous partners was probed. Endogenous Jab1/MIF complexes were precipitated from untreated 293T cells. Specific coprecipitation of MIF was detected by anti-MIF Western blot when anti-Jab1 antibody but not control antibody was [sued] *used* for coprecipitation. Thus, MIF specifically binds to $p38^{Jab1}$ both in vivo and in vitro.

Figure 2:
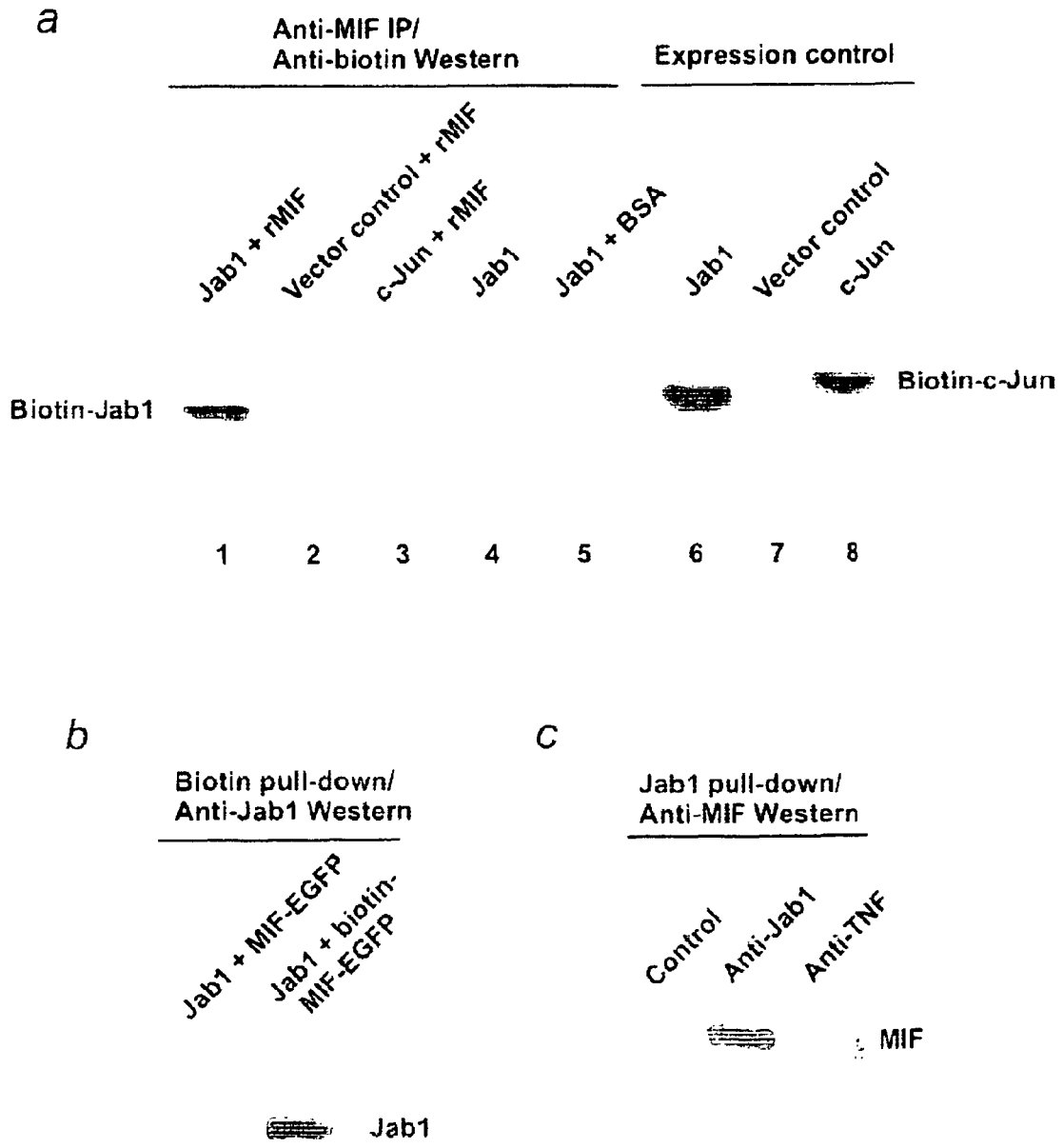
FIG. 2 shows that MIF specifically interacts with Jab1.

FIG. 2 shows that MIF specifically interacts with Jab1. a, Interaction in vitro. Complexes of rMIF and biotin-Jab1 expressed in TNT lysates were precipitated by MIF-specific antibody, and biotinylated proteins detected by Western blotting (left panel). Right panel, expression control. b, Interaction of immobilised MIF with Jab1. Streptavidin bead-immobilised TNT-translated biotin-MIF-EGFP or unlabelled control was incubated with TNT-translated Jab1, complexes isolated, and Jab1 detected by immunoblotting. c, Interaction of MIF and Jab1 in vivo. Endogenous Jab1/MIF complexes were immunoprecipitated from 293T cell lysates with anti-Jab1 antibody and MIF detected by immunoblotting. Precipitation with anti-TNF antibody or beads alone served as controls.

EXAMPLE 3

Detecting Interaction of MIF with Jab Using Modulation of AP-1-Dependent Reporter Gene Activity.

Transcriptional coactivator function of Jab1 is due to enhancement of AP-1 transcriptional activity. It was tested whether MIF, by binding to Jab1, could modulate this activity. AP-1 dependent reporter gene activity in 293T cells transiently expressing the collagenase TRE luciferase reporter was measured.

The effects of MIF were assessed by measuring AP-1-dependent reporter gene activity in transfected 293T cells using the 5×TRE-luciferase reporter. Recombinant MIF, in a concentration-dependent manner, fully reversed TNF-α-induced AP-1-dependent reporter gene activity and, at a concentration of 1 μM, fully inhibited potentiation of AP-1 reporter gene activity induced by $p38^{Jab1}$ which had been transiently cotransfected into cells as full-length cDNA together with the addition of rMIF. Inhibition of AP-1 activity by MIF was not a secondary effect of MIF-mediated altered cell growth. Significant potentiation by $p38^{Jab1}$ (2-fold) was observed in the absence of transfected c-Jun, indicating that endogenous c-Jun levels were sufficient for potentiation by $p38^{Jab1}$ to occur. Inhibition by MIF was already significant at 1 pM (~30%) and was complete when 10 nM-1 μM rMIF were applied.

Figure 3:
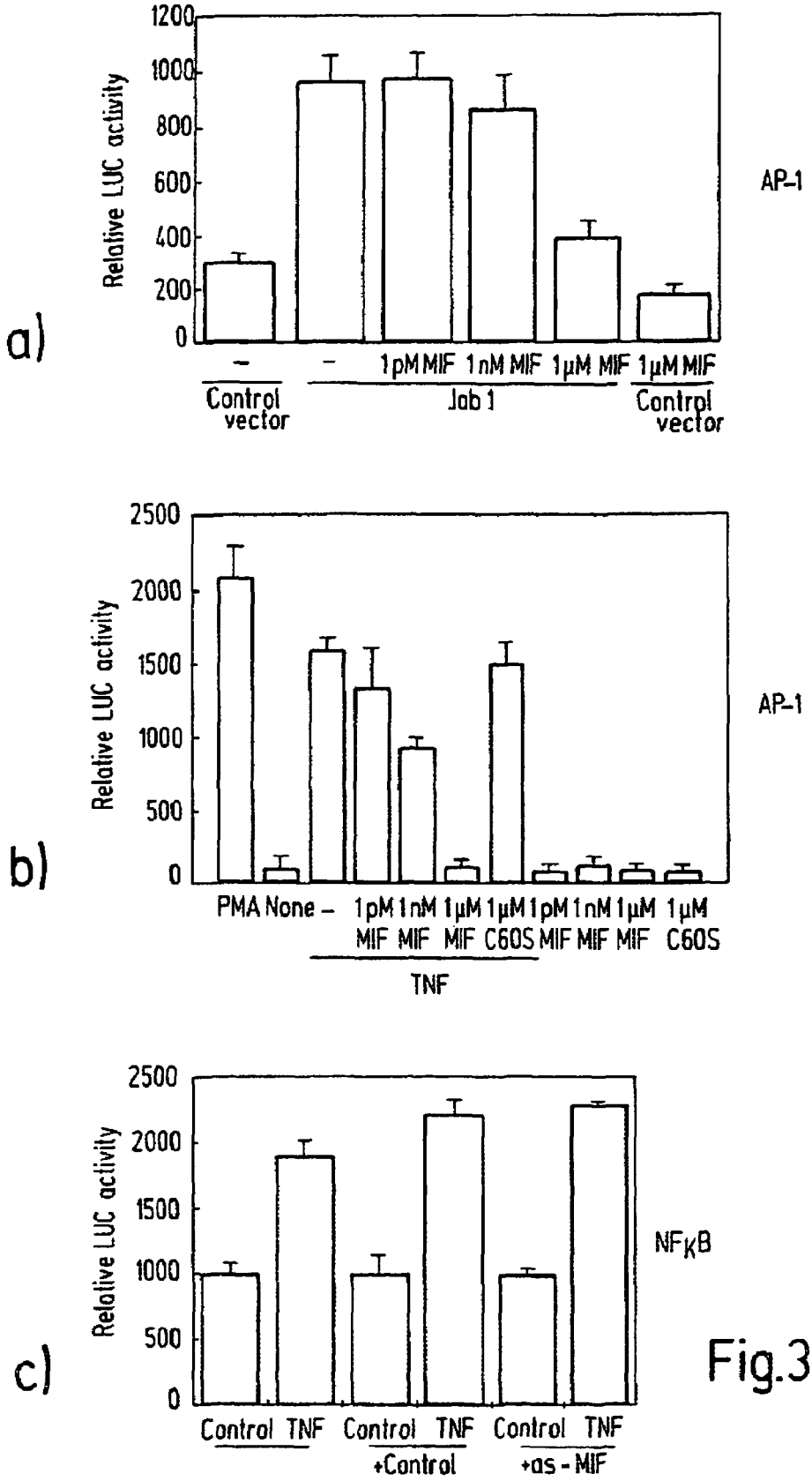
FIG. 3 shows that MIF inhibits stimulated AP-1 activity.

FIG. 3 shows that MIF inhibits stimulated AP-1 activity. a, MIF inhibits Jab1-mediated activation of AP-1 reporter gene activity in 293T cells. Transfections with pCI-neo-Jab1 or control vector are compared with or without (−) rMIF. b, MIF inhibits TNF-induced AP-1 activity. Same as a, but with TNF instead of Jab1 induction. Stimulation by PMA was a control. Data represent means±SD of four determinations and are representative of three experiments. c, MIF does not inhibit stimulated NFκB reporter gene activity. TNF-induced NFKB from antisense MIF macrophages with reduced content of endogenous MIF (+as-MIF) is compared with activities of control (+control) and non-transfected (−) cells. The mean±SD of 3 measurements is given. LUC, relative luciferase activity.

Figure 4:
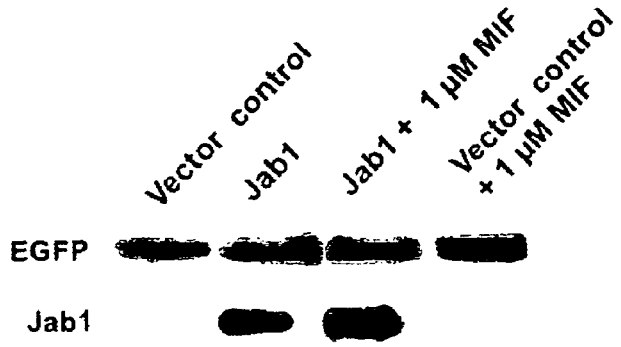
FIG. 4 shows that MIF inhibits potentiation of AP-1 reporter gene activity (collagenase 5×12-o-tetradecanol phorbol acetate response element (TRE) promoter) by Jab1 and UV stress.
Figure 4:
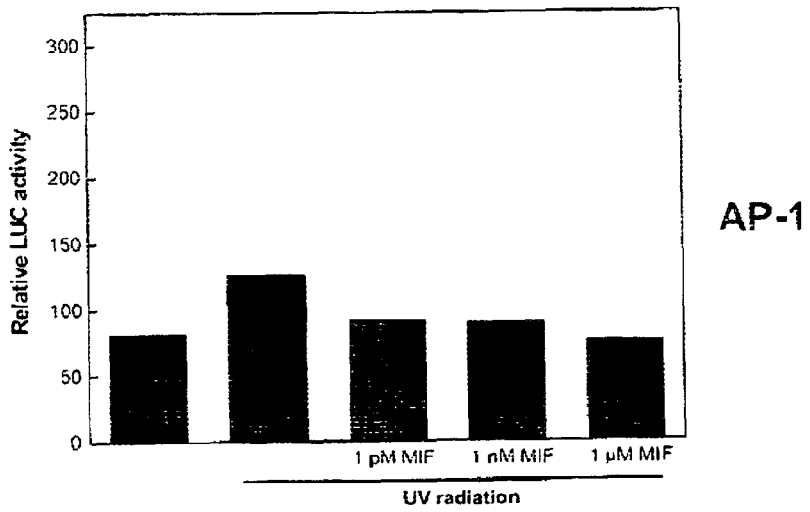
Figure 4:
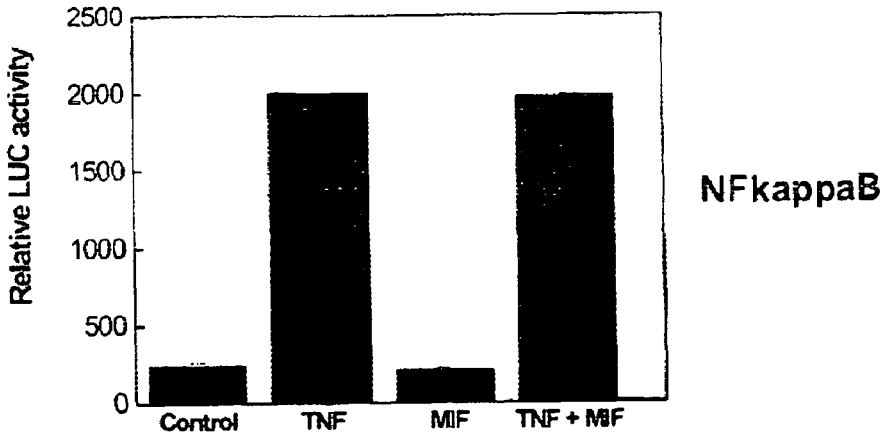

FIG. 4 shows that MIF inhibits potentiation of AP-1 reporter gene activity (collagenase 5×12-o-tetradecanol phorbol acetate response element (TRE) promoter) by Jab1 and UV stress. 293T cells were transfected with the reporter plasmids and, where indicated, cotransfected with pCI-neo-Jab1 or empty control vector and incubated with the indicated concentrations of rMIF or buffer control for 18 h. a, Western blotting control experiment for FIG. 3a displaying analysis of Jab1 overexpression and control EGFP cotransfection by anti-Jab1 and antiGFP-Western. The co-transfected EGFP construct (pN3-EGFP, Clontech) was added at 0.05 μg per incubation. In addition, EGFP-positive cells were counted at the end of the incubation. Transfection efficiencies judged by this analysis was 45-50% for FIGS. 3a and 35-45% for FIG. 3b. An effect of MIF itself on 293T cell growth under the conditions of the assay was excluded by additional cell counts. Wells after the end of the incubation period contained 2.3-2.5×10 5 cells (FIGS. 3a) and 3.8-4.1×10 4 cells (FIG. 3b). Results are expressed as relative luciferase (LUC) activity. b, MIF inhibits UV stress-induced AP-1 transcriptional activity. Same as FIG. 3b, but with UV light induction (Stratalinker, 3.6 Joule/cm 2 , 20 min+90 min) instead of TNF treatment. Data represent the mean±SD of 4 measurements. c, MIF does not interfere with stimulated NFkappaB activity. Recombinant MIF (rMIF) does not inhibit TNF-induced NFkappaB reporter gene activity in 293T cells. Cells were transfected with the reporter plasmids and incubations with rMIF (40 h) performed at a concentration of 1 μM. TNF was added at a concentration of 10 ng/ml (6 h). Results are relative luciferase (LUC) activities and represent the mean±SD of 3 determinations.

MIF also inhibits TNF- and UV-stress-induced AP-1 transcriptional activity. Neither exogenously added nor endogenously MIF interferes with NFκB activity. Recombinant MIF (1 μM) has no effect on TNF induced NFκB reporter gene activity in 293T cells.

EXAMPLE 4

Detecting Interaction of MIF with Jab1 Using Electromobility-Shift Assay (EMSA).

A transcriptional co-activator function by $p38^{Jab1}$ is due to enhancement of the binding of c-Jun to the AP-1 site. Thus, it was assumed that MIF, by binding to $p38^{Jab1}$, could modulate this activity. Such an effect on DNA binding was assessed by performing electromobility-shift assay (EMSA) on nuclear extracts from 293 cells that had been transfected with $p38^{Jab1}$ and/or c-Jun and that had been incubated in the presence or absence of rMIF, using the 12-o-tetradecanol phorbol acetate response element (TRE). $p38^{Jab1}$ promoted binding of c-Jun to the TRE. When MIF was incubated with cells overexpressing both $p38^{Jab1}$ and c-Jun, a marked inhibition (2-fold) of the activatory effect of $p38^{Jab1}$ on the binding of c-Jun to the AP-1 site was seen. By contrast, when only one or none of the transcriptional factors was overexpressed, MIF exhibited a small activatory effect, but this effect was not seen in EMSA from programmed reticulocyte lysates. EMSA from nuclear extracts of the HeLa Tet-off cell line HtTA, which stably expresses the tetracycline-controlled transactivator system and into which the human MIF cDNA was stably transfected to overexpress the MIF protein 5-6-fold over endogenous MIF following removal of doxycyclin, confirmed that MIF can significantly inhibit AP-1-dependent DNA shifts. The degree of inhibition in this system is probably even more marked, because the band intensity in the doxycyclin-repressed incubation likely represents a DNA shift that is already inhibited by the significant concentrations of endogenous MIF (~100 fg/cell).

EXAMPLE 5

MIF and $p38^{Jab1}$ Regulate Cell Signalling Pathways

To test whether $p38^{Jab1}$ and MIF could act to more broadly regulate cell signalling pathways, regulation of AP-1 activity by mechanisms upstream of direct transcriptional control was investigated. It was considered that $p38^{Jab1}$ may modulate JNK activity. Transient transfections of 293 cells with $p38^{Jab1}$ revealed that immuno-precipitated kinase activity on GST-c-Jun(1-79) was markedly stimulated by $p38^{Jab1}$. Enhancement by $p38^{Jab1}$ was 2-3-fold and was stronger than N-terminal phosphorylation of GST-c-Jun(1-79) following stimulation with standard concentrations of TNF-α. It was investigated whether MIF would also inhibit this $p38^{Jab1}$-mediated effect. Recombinant MIF, in a dose-dependent fashion, completely reversed enhancement of JNK activity by $p38^{Jab1}$. Thus, recombinant MIF reversed enhancement of JNK activity by Jab1. 200 nM MIF or more led to complete inhibition. Similarly, TNF-α-induced JNK activity was suppressed to baseline levels following treatment with rMIF. The MIF-$p38^{Jab1}$ interaction should occur independently of whether MIF is endogenously overexpressed or exogenously added to cells. This was verified tested by transient transfection experiments, where TNF-α- or $p38^{Jab1}$-induced JNK activity was measured in 293 cells that had been co-tranfected with MIF-EGFP or EGFP alone. Similar to the exogenously added rMIF, the endogenously overexpressed MIF fully suppressed both TNF-α- and $p38^{Jab1}$-mediated activation of JNK.

Figure 5:
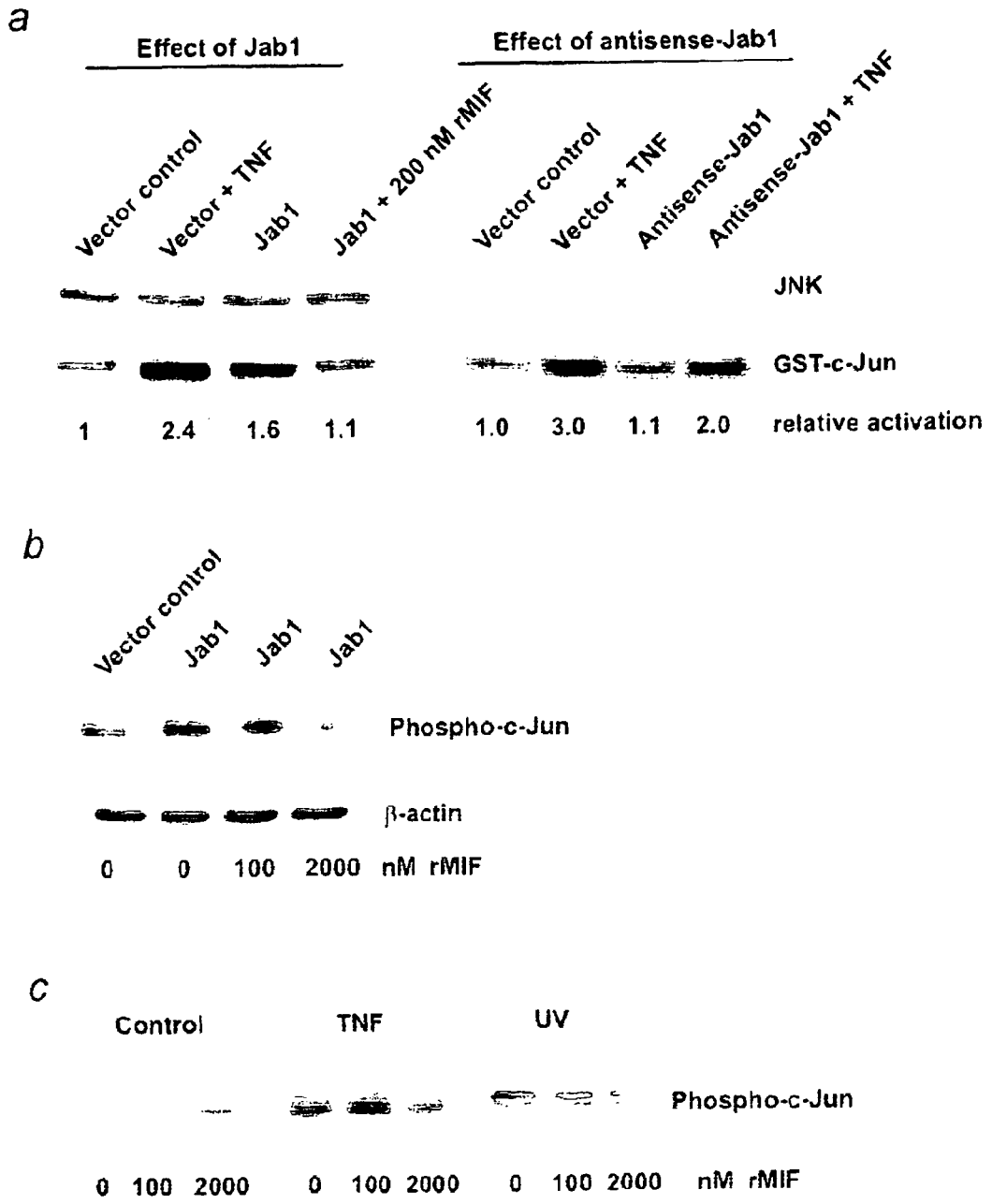
FIG. 5 shows Jab1 enhances JNK activity and phospho-Jun levels and MIF inhibits these effects.

FIG. 5 shows that Jab1 enhances JNK activity and phospho-c-Jun levels and MIF inhibits these effects. a, rMIF inhibits Jab1-mediated enhancement of JNK activity. Left, comparison of phosphorylation of GST-c-Jun(1-79) by JNK immunoprecipitates from 293T cells transfected with pCI-neo-Jab1 versus empty vector and treated with rMIF or buffer. Relative activation indicates band intensities. Control, TNF induction. Right, as left but cotransfection of antisense-Jab1 plasmid where indicated (control, immunoblots of JNK levels; transfection efficiences: 40-50%; variances: ±10%; induction of JNK by Jab1: 1,6-fold±SD of 0.08; n=3). b, Inhibition by MIF of Jab1-induced phosphorylation of endogenous c-Jun. Incubations as in 4a but immunoblots of phospho-c-Jun analysed. Betaactin immunoblots served as control. C, As b, but phosphorylation of c-Jun induced by TNF or UV stress.

Figure 6:
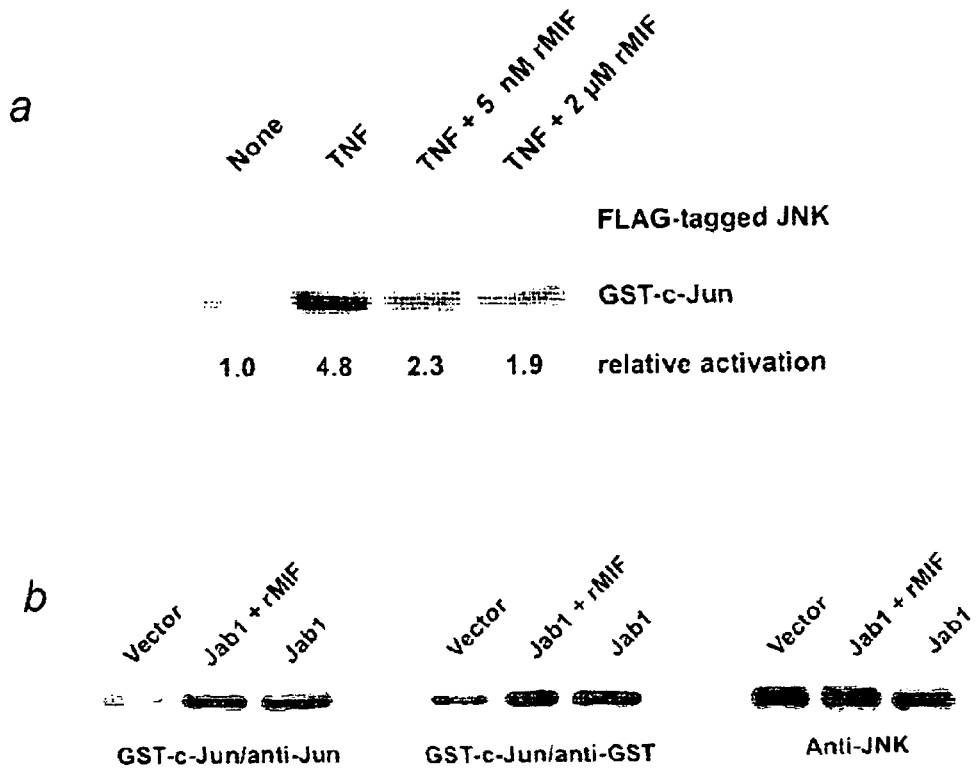
FIG. 6 shows modulation of JNK by Jab1 and MIF.

FIG. 6 shows modulation of JNK by Jab1 and MIF. a, Inhibition of TNF-stimulated JNK activity by rMIF. 293T cells were transfected with FLAG-tagged JNK-coding vector and incubated with TNF (20 ng/ml) and rMIF or buffer control as indicated for 48 h. JNK immunoprecipitates were used to phosphorylate GST-c-Jun(1-79) and relative band intensities (indicated as relative activation) estimated by phosphoimage scanning. Control Western blots were analysed by anti-FLAG-antibody. Variances were generally in the range of ±10%. b, Enhancement of the binding of JNK to c-Jun beads by Jab1 but absence of interference by MIF. Possible effects of Jab1 and MIF on the binding avidity of c-Jun to JNK were investigated by analysing the effect of Jab1 overexpression and MIF coincubation on the binding of endogenous JNK to GST-c-Jun(1-79) beads in lysates from 293T cells. Transfection of cells with Jab1 led to an enhanced binding of JNK to c-Jun beads compared to control-transfected cells. Addition of rMIF did not influence this Jab1 effect. 293T cells were transfected with Jab1 vector as in FIG. 4a of the manuscript and cell lysates incubated with GSH agarose-bound GST-c-Jun(1-79). Eluted complexes were incubated and precipitated with anti-JNK antibody in the presence or absence of rMIF and bound proteins analysed by anti-JNK (internal control), anti-GST, and anti-c-Jun Western blotting.

EXAMPLE 6

To investigate whether MIF could also negatively regulate Jab1 action with regard to non-AP-1-related activities, the effect of MIF on the cell cycle inhibitor $p27^{Kip1}$ which binds to Jab1 and whose degradation is instigated by Jab1 was studied. Contrary to Jab1, which suppresses $p27^{Kip1}$ levels, MIF, in a dose-dependent manner, induced $p27^{Kip1}$ levels, as indicated by immunoblots prepared from lysates of proliferating NIH 3T3 fibroblasts and Jurkat T cells. This induction was Jab1-dependent as $p27^{Kip1}$ levels did not rise in response to rMIF when cells were transfected with antisense Jab1 construct which almost completely suppressed endogenous Jab1 protein. $p27^{Kip1}$ induces G1 growth arrest and Jab1 can rescue serum-starved fibroblasts from growth arrest. It was found that overexpressed MIF-EGFP or exogenous rMIF, in a concentration-dependent manner, inhibited both Jab1-induced reduction of serum dependence of fibroblasts and growth of proliferating fibroblasts. As MIF did not directly bind to $p27^{Kip1}$, did not stimulate $p27^{Kip1}$ mRNA or protein synthesis, and as Jab1 promotes the proteasome-dependent degradation of $p27^{Kip1}$, effects of MIF in the context of $p27^{Kip1}$ degradation were analysed. $p27^{Kip1}$ levels, when measured by immunoprecipitation from synchronised, pulse-chase-labelled fibroblasts were higher in the presence of added rMIF. The stabilising effect of MIF on $p27^{Kip1}$ levels was not further enhanced by addition of the proteasome inhibitor LLnL. By contrast, enhancement of $p27^{Kip1}$ levels by MIF alone was even more pronounced than by LLnL alone. At the same time, addition of MIF slightly increased $p27^{Kip1}$ levels in the presence of a protein synthesis blocker. As coimmunoprecipitation studies indicated that MIF partially interfered with $p27^{Kip1}$/Jab1 complex formation, these data show that MIF-mediated effects mirror $p27^{Kip1}$-mediated growth arrest and that this occurs via inhibition of Jab1-dependent degradation of $p27^{Kip1}$.

Figure 7:
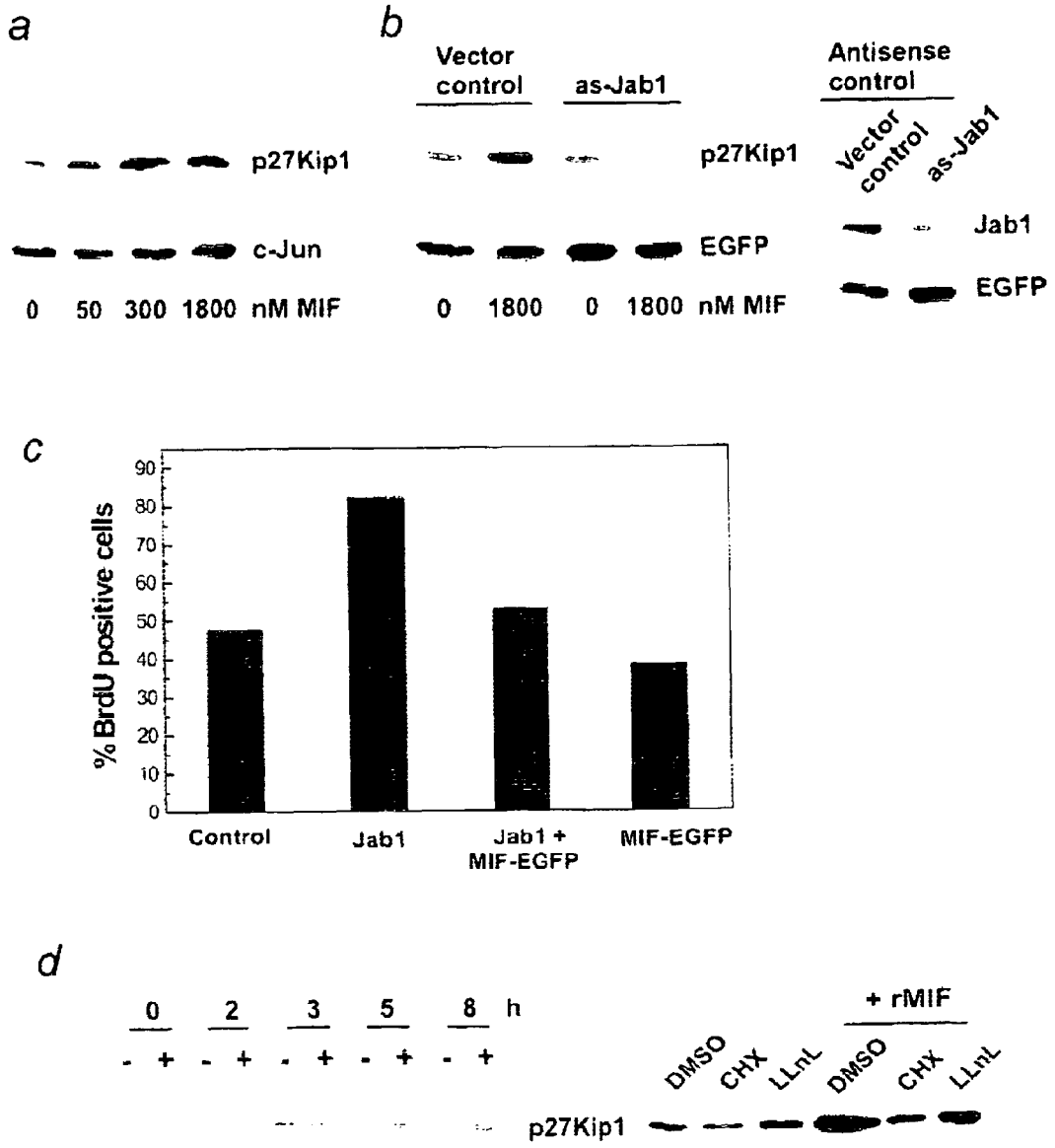
FIG. 7 shows that MIF stabilises $p27^{kip1}$ protein and inhibits fibroblast growth in a Jab1-dependent manner.

FIG. 7 shows that MIF stabilises $p27^{Kip1}$ protein and inhibits fibroblast growth in a Jab1-dependent manner. a, MIF induces $p27^{Kip1}$ expression in fibroblasts ($p27^{Kip1}$ immunoblots and c-Jun control blots). b, $p27^{Kip1}$ induction by MIF is Jab1-dependent. Left, As a, but additional transfection of antisense Jab1 or control plasmid (efficiency control, pEGFP cotransfection. Right, The antisense construct reduces Jab1 in fibroblasts. c, Inhibition by MIF of Jab1-mediated reduction of serum dependence of fibroblasts. Proliferation of GFP-expressing cells is analysed in Jab1- and MIF-EFGP-overexpressing versus control vector-treated cells via BrdU incorporation. Data are means±SD of four determinations. d, MIF inhibits proteasome-mediated degradation of $p27^{Kip1}$. Left, MIF reduces degradation of $p27^{Kip1}$ in pulse-chase labelled fibroblasts. [35S]$p27^{Kip1}$ levels shown from immunoprecipitations from rMIF-(+) versus buffer-treated cells. Right, MIF effect is proteasome-linked. As a, but incubations followed by treatment with DMSO, cycloheximide (CHX), or LLnL.

Figure 8:
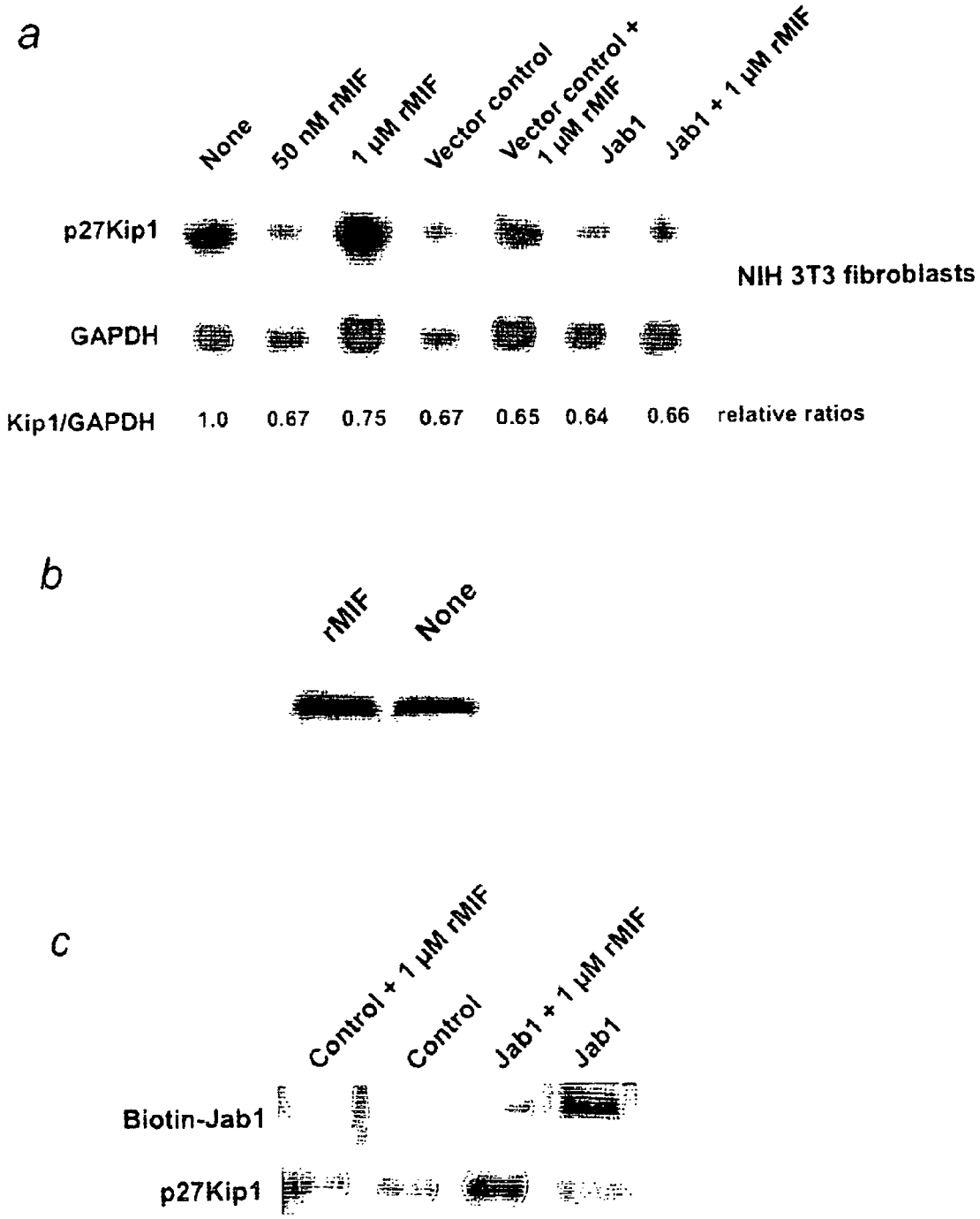
FIG. 8 shows the mechanism of $p27^{kip1}$ induction by MIF.

FIG. 8 shows the mechanism of p27 Kip1 induction by MIF. a, Effect of rMIF on $p27^{Kip1}$ mRNA levels as analysed by Northern blotting. 1×10 7 NIH 3T3 fibroblasts were incubated in the presence or absence of rMIF (as indicated) for 40 h, cells washed in ice-cold PBS, and lysed in Trizol reagent (Gibco BRL, Life Technologies). Total cellular RNA was isolated by the Trizol protocol, RNA quantitated, and applied to a standard Northern blotting procedure (Burger-Kentischer et al., Kidney Int. 55, 1417-1425, 1999). Probes were generated by the PCR-based DIG-labelling method (Roche Diagnostics). The Kip probe corresponded to bases 8-181 of mouse Kip1 (Genbank accession number U09968) and the human GAPDH probe was as described in Burger-Kentischer et al. For transfections, cells were incubated with the plasmids pjabl and pClneo for 5 h and rested for 1 h before rMIF was added. Kip mRNA levels were found to be at comparable levels independent of whether fibroblasts were incubated with increasing concentrations of rMIF. Overexpression of Jab1 following transient transfection of the pJab1 vector also did not lead to a stimulatory effect of MIF on Kip RNA formation. A similar result was obtained when mRNA levels of Kip were analysed in Jurkat T cells (Kip/GAPDH ratios were: buffer, 1.0; 100 nM rMIF 0.8; 1 μM rMIF, 0.78). b, Effect of rMIF on p27 Kip1 protein synthesis. $4\times10^6$ NIH 3T3 fibroblasts were synchronised by an overnight incubation in media containing 1% FCS, rMIF (1 μM) or control buffer were added, and cells incubated for another 36 h. Cells were washed in cysteine/methione-free media, incubated for 15 min in this media. and radioactivity (PROMIX, Amersham-Pharmacia Biotech) added. Cells were incubated for 60 min in the presence of the label, washed and Kip immunoprecipitated with anti-Kip antibody. Samples were electrophoresed in a 13% SDS-PAGE gel and radioactivity detected by a phoshoimager. c, Effect of recombinant MIF on formation of Kip/Jab1 complexes in fibroblasts. NIH 3T3 fibroblasts were either incubated with LLnL for 4 h. Biotin-Jab1 was overexpressed in TNT reticulocyte lysates. For control, TNT lysates were programmed with the pClneo control vector and aliquots from both lysates added to fibroblast lysates as indicated. Recombinant MIF (1 μM) or control buffer was added and the mixtures incubated for 2 h at coimmunoprecipitation conditions. Complexes were precipitated with anti-Kip antibody (Santa Cruz). Immunoblots stained for either biotin-Jab1 (upper panel) or Kip1 (control, lower panel) were then performed to evaluate the potential effect of MIF on Kip/Jab complex formation.

EXAMPLE 7

Mutant Analysis and Competition Experiments.

To investigate more closely those structural parts of MIF which are essential for Jab1 binding and modulation, mutants were created. One mutant is mutant C60SMIF wherein in the wildtype MIF sequence the cysteine at position 60 has been replaced by a serine residue. Other mutants are MIF (50-65) which is a peptide fragment of wildtype MIF consisting of the 16 amino acid residues being present at position 50-65 of wildtype MIF.

Mutant $Ser^{57}$ $Ser^{60}$ MIF(50-65) represents a mutant consisting of the wildtype amino acid residues at positions 50-65 of wildtype MIF wherein at position 57 a serine and in position 60 another serine has been inserted instead of the wildtype amino acids Cys at that position. The above given positions of amino acids are given in correlation with the published human MIF sequence described in Kleeman et al., FIG. 2 (1998 b) whose disclosure content is with respect to the amino acid sequence of MIF and its preparation wholly included in the disclosure of the present teaching.

Mutant C60SMIF exhibits a clear structure activity profile. This mutant can be readily folded for use in activity assays but is devoid of the enzymatic oxidoreductase and immunological activity of MIF. It was found that C60SMIF, while capable of binding to biotin-Jab1, did not inhibit TNF-induced AP-1 activity, did not reduce Jab1-induced enhancement of c-Jun DNA binding, and exhibited reduced $p27^{Kip1}$- inducing properties. Cys60-spanning 16 residue MIF peptide, MIF (50-65) and $Ser^{57}$ $Ser^{60}$ MIF (50-65) strongly competed with wildtype MIF for Jab1 binding, indicating together that this region is involved in the binding and modulation of Jab1.

Figure 9:
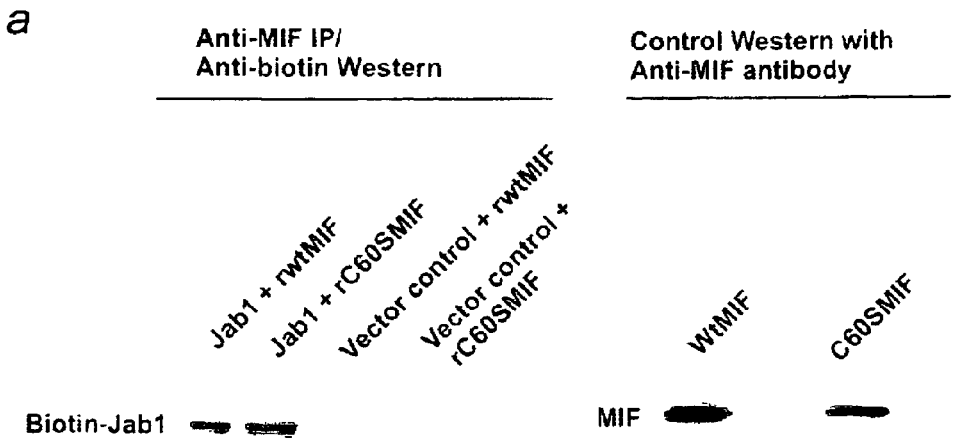
FIG. 9 shows the chacterisation of the binding site between MIF and Jab1.
Figure 9:
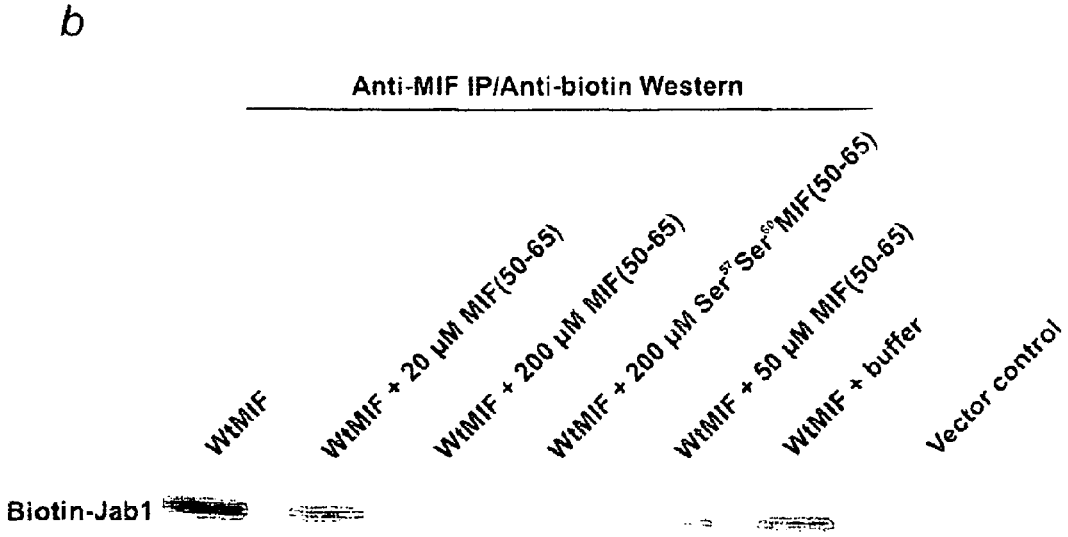
Figure 9:
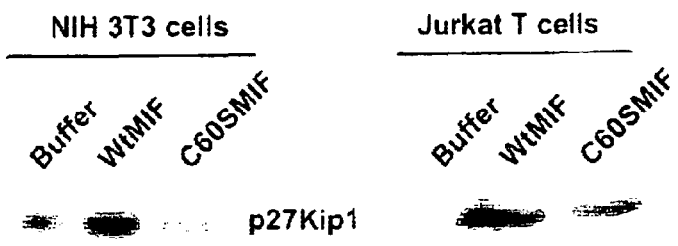

FIG. 9 shows the characterisation of the binding site between MIF and Jab1. Sequence (50-65) of MIF but not the Cys60 residue alone is critical for interaction between MIF and Jab1. a, To investigate whether mutant C60SMIF also bound to Jab1, binding of rC60SMIF (r: recombinant) to biotin-labelled Jab1 was compared with that of rwtMIF in vitro in the TNT reticulocyte lysate. An anti-biotin S—HRP Western blot is shown (left panel). Direct Western blotting analysis of rwtMIF and rC60SMIF verified that the anti-MIF antibody used for coimmunoprecipitation exhibited comparable binding properties to both proteins (right panel). b, MIF peptide (50-65), in a concentration-dependent manner, competes with wildtype MIF for binding of biotin-Jab1 in vitro in the TNT reticulocyte lysate system. An anti-biotin S—HRP Western blot is shown. An analogue of the MIF (50-65) peptide with the two Cys residues substituted for Ser was also tested and also competed for Jab1 binding, confirming that the CALC Cys residues themselves (see a) are not critical for binding of Jab1. c, Mutant C60SMIF only showed reduced p27 Kip1-inducing properties as compared to wildtype MIF. Anti-Kip1 Western blots from lysates of NIH 3T3 fibroblasts and Jurkat T cells incubated with rMIF or mutant C60SMIF (20 nM) are shown.

Figure 10:
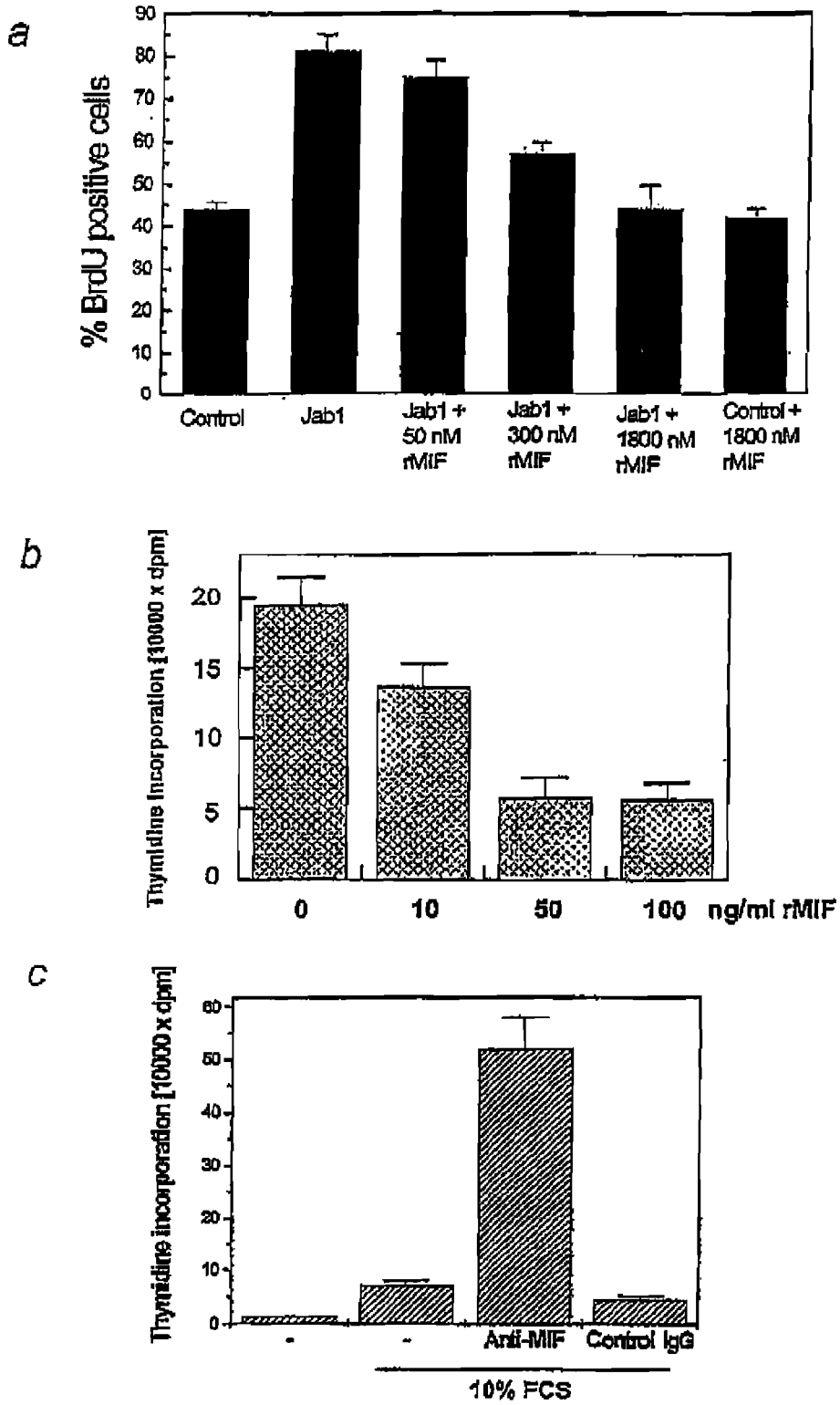
FIG. 10 shows the effect of MIF on growth arrest of fibroblasts.
Figure 10:
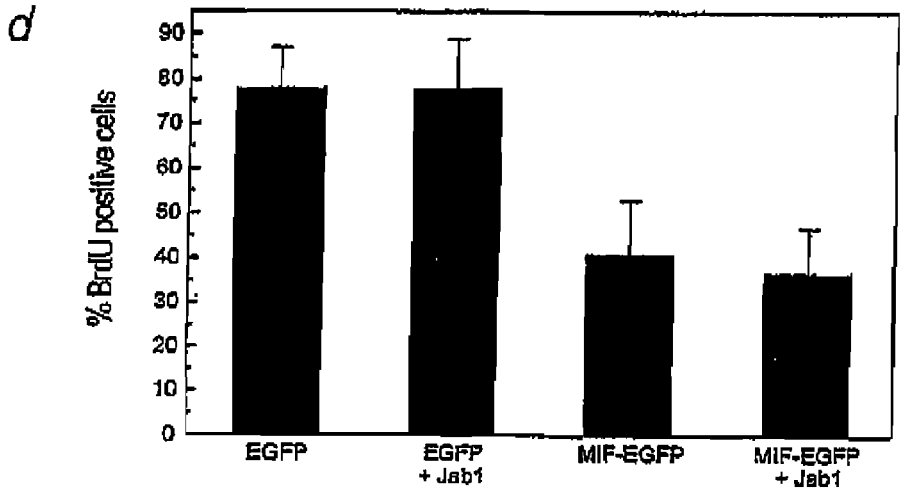

FIG. 10 shows the effect of MIF on growth arrest of fibroblasts. a, Effect of exogenously added rMIF on Jab1-mediated rescue of fibroblasts from starvation. NIH 3T3 fibroblasts were transfected with Jab1 or control vector and cotransfected with EGFP. Cells were serum-starved for 2 h, rMIF added at the indicated concentrations, cells starved for another 36 h, incubated with BrdU for 18 h, and stained with anti-BrdU antibody. Only GFP-expressing cells were analysed. Data represent the mean±SEM of 4 determinations (>150 cells each) and are representative of 3 independent experiments. Exogenously added rMIF inhibited the Jab1 effect in a dose-dependent manner. With 1.8 μM rMIF added a similar degree of inhibition was obtained as seen when EGFP-MIF was transfected (inhibition from −80% to 40%; see manuscript). b, Effect of rMIF on starvation-induced growth arrest of fibroblasts. Semi-confluent NIH 3T3 fibroblasts were synchronized by incubation in serum-free medium for 24 h. Culture medium was changed to medium with 0.5% FCS, containing either no further addition or rMIF at the indicated concentration. Incubation was continued in the presence of labelled thymidine for 16 h. FIG. 10 is representative of two independent experiments and the data represent the mean±SD of 6 measurements. c, Effect of anti-MIF antibody on cell growth of proliferating or serum-starved fibroblasts. Semi-confluent 3T3 cells were synchronized by incubation in serum-free medium for 24 h. Medium was changed to either serum-free (latter not shown) or 10% FCS-containing medium, containing either no further addition or 200 μg/ml of polyclonal anti-MIF antibody or 200 μg/ml unrelated rabbit IgG as control. Incubation was continued in the presence of labelled thymidine for 16 h. FIG. 10 shows one of four experiments, using anti-MIF IgG in combination with 10% FCS. Similar results were obtained when following synchronization, incubations were continued in serum-free media. d, Effect of endogenously overexpressed MIF on the growth of proliferating fibroblasts. NIH 3T3 fibroblasts were synchronized by incubation in media containing 0.5% serum for 18 h. Cells were switched to full-serum media conditions, transfected with Jab1 or control vector and EGFP-MIF or EGFP, and incubated for another 40 h. The percentage of BrdU-positive cells was assessed as before. Data represent the mean±SD of 4 determinations and are representative of 3 independent experiments.

REFERENCES

1. Bernhagen, J. Calandra, T., & Bucala, R. Regulation of the immune response by macrophage migration inhibitory factor: biological and structural features. J. Mol. Med. 76, 151-161 (1998).
2. Bernhagen, J. et al. MIF is a pituitary-derived cytokine that potentiates lethal endotoxaemia. Nature 365, 756-759 ([1193] *1993*).

3. Calandra, T. et al. MIF as a glucocorticoid-induced modulator of cytokine production. Nature 377, 68-71 (1995).
4. Donnelly, S. C. et al. Regulatory role for macrophage migration inhibitory factor in acute respiratory distress syndrome. Nature Med. 3, 320-323 (1997).
5. Kleeman, R. et al. Disulfide analysis reveals a role for macrophage migration inhibitory factor (MIF) as a thiol-protein oxidoreductase. J. Mol. Biol. 280, 85-102 (1998 a).
6. Kleeman, R., Kapurniotu, A, Mischke, R. Held, J. & Bernhagen, J. Characterization of catalytic center mutants of macrophage migration inhibitory factor (MIF) and comparison with C81S MIF. Eur. J. Biochem. 261, 753-766 (1999).
7. Rosengren, E. et al. The immunoregulatory mediator migration inhibitory factor (MIF) catalyzes a tautomerization reaction. Mol. Med. 2, 143-149 (1996).
8. Claret, F.-X Hibi, M. Dhut, S. Toda, T. & Karin, M. A new group of conserved coactivators the increase the specificity of AP-1 transcription factors. Nature 383, 453-457 (1996).
9. Tomoda, K. Kubota, Y & Kato, J-Y. Degradation of the cyclin-dependent-kinase inhibitor $p27^{Kpi1}$ is instigated by Jab1. Nature 398, 160-164 (1999).
10. Bacher, M. et al. Migration inhibitory factor expression in experimentally induced endotoxemia. Am. J. Pathol. 15, 235-246 (1997).
11. Fields, S. & Song, O. A novel genetic system to detect protein-protein interactions. Nature 340, 245-246 (1989).
12. Bacher, M. et al. MIF expression in the rat brain—implications for neuronal function. Mol. Med. 4, 217-230 (1998).
13. Ogata, A. Nishihira, J. Suzuki, T. Nagashima, K. & Tashiro, K. Identification of macrophage migration inhibitory factor mRNA expression in neural cells of the rat brain by in situ hybridization. Neurosci. Lett. 246, 173-177 (1998).
14. Bernhagen, J. et al. Purification, bioactivity, and secondary structure analysis of mouse and human macrophage migration inhibitory factor (MIF). Biochemistry 33, 14144-14155 (1994).
15. Sun, H., Bernhagen, J., Bucala, R. & Lolis, E. Crystal structure at 2.6 Å resolution of human macrophage migration inhibitory factor. Proc. Natl. Acad. Sci. USA 93, 5191-5196 (1996).
16. Seeger, M. et al. A novel protein complex involved in signal transduction possessing similarities to 26S proteasome subunits. FASEB J. 12, 469-478 (1998).
17. Hofmann, K. & Bucher P. The PCI domain: a common theme in three multiprotein complexes. Trends Biochem. Sci. 23, 204-205 (1998).
18. Asano, K. et al. Structure of cDNAs encoding human eukaryotic initiation factor 3 subunits. J. Biol. Chem. 272, 27042-27052 (1997).
19. Karin, M. The regulation of AP-1 activity by mitogen-activated protein kinases. J. Biol. Chem. 270, 16483-16486 (1995).
20. Hirota, K. et al. AP-1 transcriptional activity is regulated by a direct association between thioredoxin and Ref-1. Proc. Natl. Acad. Sci. USA 94, 3633-3638 (1997).
21. Wilhelm, D., Bender, K., Knebel, A. & Angel, P. The level of intracellular glutathione is a kex factor for the induction of stress-activated signal transduction pathways including Jun N-terminal protein kinases and p38 kinase by alkylating agents. Mol. Cell. Biol. 17, 4792-4800 (1997).
22. Lanathan, A., Williams, J. B., Sanders, L. K. & Nathans, D. Growth factor-induced delayed early response genes. Mol. Cell. Biol. 12, 3919-3929 (1992).
23. Wistow, G. J., Shaughnessy, M. P., Lee, D. C., Hodin, J. & Zelenka, P. S. A macrophage migration inhibitory factor is expressed in the differentiating cells of the eye lens. Proc. Natl. Acad. Sci. USA 90, 1271-1280 (1993).
24. Scheinman, R. I., Cogswell, P. C., Lofquist, A. K. & Baldwin, A. S.;. Role of transcriptional activation of IκBα in mediation of immunosuppression by glucocorticoids. Science 270, 283-289 (1995).
25. Mitchell, R. A. Metz, C. N., Peng, T. & Bucala, R. Sustained mitogen-activated protein kinase (MAPK) and cytoplasmic phospholipase A2 activaion by macrophage migration inhibitory factor (MIF). Regulatory role in cell proliferation and glucocorticoid action. J. Biol. Chem. 274, 18100-18106 (1999).
26. Dedio, J., Jahnen-Dechent, W., Bachmann, M. & Muller-Esterl, W. The multiligand-binding protein gC1qR, putative C1q receptor, is a mitochondrial protein. J. Immunol. 160, 3534-3542 (1998).
27. Johannes, F. J. et al. Protein kinase Cu down-regulation of tumor-necrosis-factor-induced apoptosis correlates with enhanced expression of nuclear-factor-kappaB-dependent protective genes. Eur.J. Biochem. 257, 47-54 (1998).
28. Angel, P. et al. Phorbol ester-inducible genes contain a common cis element recognized by a TPA-modulated transactivating factor. Cell 49, 729-736 (1987).
29. Berberich, I. et al. Cross-linking CD40 on B cells preferentially induces stress-activated protein kinases rather than mitogen-activated protein kinases. EMBO J. 15, 92-101 (1996).
30. Roger et al. Increased AP-1 and NFκB activity and increased stability of IL-8 mRNA are implicated in super-induction of IL-8 mRNA by H292 cells. Biochem. J. 330, 429-435 (1998)
31. Waeber et al. Insulin secretion is regulated by the glucose dependent production of islet beta cell MIF. Proc. Natl. Acad. Sci. USA 94, 4782-4-787 (1997)
32. Kleemann et al. Specific reduction of insulin disulfides by macrophage migration inhibitory factor (MIF) with glutathione and dihydrolipoamide: potential role in cellular redox processes. FEBS Lett. 430, 191-196 (1998 b).

SEQUENCE LISTING

```
<160> NUMBER OF SEQ ID NOS: 3

<210> SEQ ID NO 1
<211> LENGTH: 16
<212> TYPE: PRT
<213> ORGANISM: Homo sapiens

<400> SEQUENCE: 1

Phe Gly Gly Ser Ser Glu Pro Cys Ala Leu Cys Ser Leu His Ser Ile
1               5                   10                  15
```

-continued

```
<210> SEQ ID NO 2
<211> LENGTH: 16
<212> TYPE: PRT
<213> ORGANISM: Homo sapiens

<400> SEQUENCE: 2

Phe Gly Gly Ser Ser Glu Pro Ser Ala Leu Ser Ser Leu His Ser Ile
1               5                   10                  15


<210> SEQ ID NO 3
<211> LENGTH: 16
<212> TYPE: PRT
<213> ORGANISM: Homo sapiens

<400> SEQUENCE: 3

Phe Gly Gly Ser Ser Glu Pro Cys Ala Leu Ser Ser Leu His Ser Ile
1               5                   10                  15
```

We claim:

[1. A method for detecting an interaction between MIF and Jab1, the method comprising a) providing a cell containing a reporter gene comprising a DNA-binding protein recognition site, wherein the reporter gene expresses a reporter protein when the reporter gene is activated by a transcriptional activation domain when the transcriptional activation domain is in sufficient proximity to the reporter gene;

b) providing a first chimeric gene that is operably linked to expression control sequences in host cells, the first chimeric gene comprising a DNA sequence that encodes a first hybrid protein, the first hybrid protein comprising:

i) a DNA-binding domain that recognizes the DNA-binding protein recognition site of the reporter gene in the cell; and ii) the MIF protein or a part thereof;

c) providing a second chimeric gene that is operably linked to expression control sequence in the host cell, the second chimeric gene comprising a DNA sequence that encodes a second hybrid protein, the second hybrid protein comprising i) the transcriptional activation domain, and ii) the Jab1 protein or a part thereof;

iii) wherein interaction between the MIF protein and the Jab1 in the cell causes the transcriptional activation domain to activate transcription of the reporter gene;

d) introducing the first chimeric gene and the second chimeric gene into the cell;

e) expressing the first hybrid protein and the second hybrid protein in sufficient quantity for the reporter gene to be activated; and f) determining expression of the reporter gene wherein the expression measures MIF-Jab1 binding.]

[2. The method of claim 1, wherein the expression of the reporter gene is determined in cells subjected to a candidate drug to be screened and compared to the expression of the reporter gene in cells not subjected to the drug.]

[3. The method of claim 1, wherein the DNA-binding domain and transcriptional activation domain are derived from transcriptional activators having separately DNA-binding and transcriptional activations domain.]

[4. The method of claim 1, wherein the DNA-binding domain is selected from the group consisting of transcriptional activators GAL4, GCN4 and ADR1.]

[5. The method of claim 1, wherein the first hybrid protein or the second hybrid protein, or the first and the second hybrid proteins, is encoded on a library of plasmids containing DNA inserts, wherein the DNA inserts are obtained from the group consisting of genomic DNA, cDNA and synthetically generated DNA.]

[6. The method of claim 1, wherein the chimeric genes are introduced into the cell in the form of plasmids.]

[7. The method of claim 1, wherein the first chimeric gene is integrated into a chromosome of the cell.]

[8. The method of claim 1, wherein the first chimeric gene is integrated into a chromosome of the cell and the second chimeric gene is introduced into the host cell as a part of a plasmid.]

[9. The method of claim 1, wherein the DNA-binding domain and the transcriptional activation domain are from different transcriptional activators.]

[10. The method according to claim 1, wherein the interaction between MIF and Jab1 is tested in the presence of a MIF competitive peptide.]

[11. The method according to claim 10, wherein the MIF competitive peptide is MIF (50-65) (SEQ ID NO: 1) or $Ser^{57}$ $Ser^{60}$ MIF (50-65) (SEQ ID NO: 2).]

[12. A method of preparing MIF comprising a) providing a first source containing MIF;

b) contacting the first source containing MIF with a second source containing isolated Jab1 under conditions allowing for the binding of MIF and Jab1; and c) separating MIF from Jab1.]

[13. The method of claim 12, wherein the first source is a cell, tissue, cell culture, cell culture supernatant, cell extract, protein preparation.]

[14. The method of claim 12, wherein the sources are disrupted by a method selected from the group consisting of sonication, chemical lysis, enzymatic lysis, and pulse or constant electrical field exposure prior to contacting the sources.]

[15. A method of preparing Jab1 comprising a) providing a first source containing Jab1;

b) contacting the first source containing Jab1 protein with a second source containing isolated MIF under conditions allowing for the binding of MIF and Jab1; and c) separating Jab1 from MIF.]

[16. The method of claim 15, wherein the first source is a cell, tissue, cell culture, cell culture supernatant, cell extract, or protein preparation.]

[17. The method according to claim 15, wherein the sources are disrupted by a method selected from the group consisting of sonication, chemical lysis, enzymatic lysis, and pulse or constant electrical field exposure prior to contacting the sources.]

[18. An isolated protein complex comprising MIF or a fragment thereof in natural association with Jab1, or a fragment thereof, optionally in natural association with a protein selected from the group consisting of, $p27^{Kip1}$, c-Jun, c-Jun-amino-terminal kinase, steroid receptor coactivator 1, integrin LFA-1, progesterone receptor and a glucocorticoid receptor.]

[19. A kit for screening candidate drugs, which kit comprises an isolated protein complex according to claim 18.]

[20. A composition comprising an isolated protein complex according to claim 18 in a pharmaceutically acceptable carrier.]

*21. An antibody that is (a) specifically reactive with MIF50-65 (SEQ ID NO: 1) and (b) is not specifically reactive to the MIF/Jab1 complex.*

*22. The antibody of claim 21, wherein the antibody is a humanized antibody.*

*23. The antibody of claim 21, wherein the antibody is a monoclonal antibody.*

*24. The antibody of claim 21, wherein the antibody is a polyclonal antibody.*

*25. The antibody of claim 21, wherein the antibody consists essentially of an antibody fragment.*

*26. The antibody of claim 21, wherein the antibody consists essentially of a Fab fragment.*

*27. The antibody of claim 21, wherein the antibody consists essentially of an Fv fragment.*

*28. The antibody of claim 21, wherein the antibody is a single chain antibody.*

* * * * *